United States Patent
Goff

(10) Patent No.: US 9,937,273 B2
(45) Date of Patent: Apr. 10, 2018

(54) METHOD OF MANAGING SPENT NUCLEAR FUEL TO IRRADIATE PRODUCTS

(71) Applicant: Russell Goff, Corvallis, OR (US)

(72) Inventor: Russell Goff, Corvallis, OR (US)

(73) Assignee: Russell Goff, Corvallis, OR (US)

( * ) Notice: Subject to any disclaimer, the term of this patent is extended or adjusted under 35 U.S.C. 154(b) by 589 days.

(21) Appl. No.: 14/070,885

(22) Filed: Nov. 4, 2013

(65) Prior Publication Data

US 2014/0126682 A1  May 8, 2014

Related U.S. Application Data

(60) Provisional application No. 61/723,279, filed on Nov. 6, 2012.

(51) Int. Cl.
| | |
|---|---|
| *G21C 19/32* | (2006.01) |
| *A61L 2/08* | (2006.01) |
| *G21F 7/015* | (2006.01) |
| *G21F 7/06* | (2006.01) |

(52) U.S. Cl.
CPC ............ *A61L 2/081* (2013.01); *G21C 19/32* (2013.01); *G21F 7/015* (2013.01); *G21F 7/06* (2013.01)

(58) Field of Classification Search
CPC . A61L 2/081; G21F 7/06; G21F 7/015; G21C 19/32
USPC ................................... 376/272, 341; 378/69
See application file for complete search history.

(56) References Cited

U.S. PATENT DOCUMENTS

| | | | | |
|---|---|---|---|---|
| 3,564,241 A | * | 2/1971 | Ludwig ..................... | G21K 5/02 250/454.11 |
| 3,641,342 A | * | 2/1972 | Armel ...................... | G21K 5/02 378/69 |
| 3,667,540 A | | 6/1972 | Kupp | |
| 4,024,406 A | * | 5/1977 | Bevilacqua ............ | G21C 19/40 376/272 |
| 4,040,480 A | * | 8/1977 | Richards .................. | G21F 5/10 376/272 |

(Continued)

OTHER PUBLICATIONS

Bruce Mincher, "Decomposition of PCbs in Oils Using Gamma Radiolysis A Treatability Study-Final Report", INEL-96/0276, Aug. 1996, pp. (iii,10,11), Idaho National Engineering Laboratory, Department of Energy, Idaho Falls, Idaho.

(Continued)

*Primary Examiner* — Jack W Keith
*Assistant Examiner* — Daniel Wasil

(57) ABSTRACT

Methods, apparatuses, and systems for the storage of spent nuclear fuel (SNF) such that a single facility can serve as both a SNF storage facility and a gamma ray irradiation facility are disclosed. In one embodiment, the SNF is encapsulated inside of a container. The SNF bearing container prevents the escape of fission products into the environment but allows the escape of gamma rays from the container. In this embodiment, several of these containers are evenly spaced throughout a room within a fortified facility and a conveyor system transports products through the room such that gamma rays emitted by the SNF deposit a desired amount of energy into the products. A passive heat removal system is formed by the coupling of the SNF bearing container to a thermal conduction element such that the SNF remains sufficiently cool even when the SNF is generating large heat loads.

3 Claims, 35 Drawing Sheets

(56) References Cited

U.S. PATENT DOCUMENTS

| | | | | |
|---|---|---|---|---|
| 4,151,419 A | * | 4/1979 | Morris | A61L 2/08 |
| | | | | 378/69 |
| 4,326,918 A | * | 4/1982 | Lapides | G21F 5/008 |
| | | | | 376/272 |
| 4,453,079 A | * | 6/1984 | Woodbridge | C02F 1/30 |
| | | | | 250/435 |
| 4,481,165 A | * | 11/1984 | Anderson | G21C 19/07 |
| | | | | 376/272 |
| 4,481,652 A | * | 11/1984 | Ransohoff | B65B 55/16 |
| | | | | 378/69 |
| 4,800,062 A | | 1/1989 | Craig | |
| 4,834,916 A | | 5/1989 | Chaudon | |
| 4,852,138 A | * | 7/1989 | Bergeret | B65B 55/16 |
| | | | | 250/453.11 |
| 5,396,074 A | * | 3/1995 | Peck | G21K 5/10 |
| | | | | 250/453.11 |
| 5,400,382 A | * | 3/1995 | Welt | G21K 5/10 |
| | | | | 378/69 |
| 5,438,597 A | | 8/1995 | Lehnert | |
| 5,799,257 A | * | 8/1998 | Meikrantz | A62D 3/172 |
| | | | | 588/406 |
| 5,832,392 A | * | 11/1998 | Forsberg | G21F 5/008 |
| | | | | 376/274 |
| 6,215,847 B1 | | 4/2001 | Perrins | |
| 6,602,314 B1 | * | 8/2003 | Sakaguchi | G21F 1/08 |
| | | | | 419/14 |
| 8,351,562 B2 | | 1/2013 | Singh | |
| 2010/0163746 A1 | * | 7/2010 | Cho | G21K 5/10 |
| | | | | 250/442.11 |
| 2013/0301767 A1 | * | 11/2013 | Loewen | G21H 5/00 |
| | | | | 376/156 |

OTHER PUBLICATIONS

L.E.Brownell, "Design of a Railway Mobile Gamma Source for Industrial Irradiations", AT(11-1)-162, Apr. 1956, pp. (vi, 26, 27), Engineering Research Institute the University of Michigan, US Atomic Energy Commission, Ann Arbor, Michigan.

* cited by examiner

METHOD OF MANAGING SPENT NUCLEAR FUEL TO IRRADIATE PRODUCTS

CROSS-REFERENCES TO RELATED APPLICATIONS

This application claims priority to U.S. Provisional Patent Application Ser. No. 61/723,279 filed on Oct. 6, 2012 entitled "Gamma Sterilization Using Spent Nuclear Fuel", the disclosure of which is hereby incorporated by reference.

BACKGROUND OF THE INVENTION

The present invention relates to a novel new way of storing the spent nuclear fuel (SNF) produced by nuclear reactors. The question of what nuclear power plants will do with their waste has always been a big issue.

When storing SNF several goals must be met:
Radioactive materials must be prevented from contaminating the environment;
The SNF rods (which constantly generates heat within them known as decay heat) must be kept cool such that the materials and structures within which the SNF is stored are not damaged, they maintain their structural integrity, and the cladding surrounding the Uranium does not degrade and create a breach in one of the first barriers to fission product release into the environment;
Personnel working in or near the facility must be protected from harmful amounts of radiation;
The nuclear fission chain reaction must be kept from becoming self sustaining (ie criticality accidents must be avoided);
Solutions to achieve the above-noted goals continue to be desired.

The present invention also relates to the field of gamma ray irradiation. Gamma ray irradiation services are in high demand and have been used for sterilizing medical supplies, killing harmful microorganisms in food stuffs, affecting the material characteristics of plastics, and many other beneficial processes. Low supplies of gamma ray sources have decreased the implementation of and increased costs associated with these beneficial gamma ray irradiation processes. Large new supplies of usable gamma ray sources continue to be desired.

The practice of creating radioactive isotopes in nuclear reactors and then using these isotopes for industrial or medical applications is relatively common in some nuclear reactors. Traditionally a small "target" comprising a non-radioactive material is placed into the nuclear reactor core to absorb neutrons and become radioactive. This "target" material is then removed from the nuclear reactor core and encapsulated in a small container such that the radioactive material does not contaminate the environment but most of its radiation can still escape and be used in industrial or medical applications.

Previous to this invention the process of using a nuclear reactor, that was built primarily for the purposes of creating electricity, to manufacture radioactive sources meant installing foreign "target" material into the reactor itself which meant several engineering analyses to ensure the foreign "target" material didn't affect the safety of the reactor. Furthermore the "targets" absorb valuable neutrons that would otherwise have been able to cause fissions in the nuclear fuel that would have created more thermal energy that could have been turned into electricity. The intrusive nature of the "targets" often affected the entire operation of the nuclear power plant and the process was typically deemed "not worth the effort" by owners of the nuclear power plants and stakeholders. Efforts have also occurred in the past to chemically separate gamma emitting radioisotopes from SNF for use in gamma sources however such processes are expensive and complicated.

SUMMARY OF THE INVENTION

Embodiments of an SNF bearing container and a novel way of recovering gamma ray resources from SNF during storage are disclosed.

The present invention involves an apparatus comprising of a thin barrier configured to be disposed between a portion of spent nuclear fuel (SNF) and an external area containing materials meant to be irradiated by gamma rays, where the thin barrier is configured to substantially prevent the release of radioisotopes found in the SNF while also being configured to allow the release of a substantially large portion of the gamma rays produced by the SNF into the external area. This thin barrier may contain a coolant disposed proximate to the thin barrier, the coolant being configured to substantially minimize the attenuation in at least one direction of gamma rays produced by the SNF. A thermally conductive element may come into thermal contact with the thin barrier, the thermally conductive element being configured to transfer at least some of the heat produced by the SNF to a heat sink. The thin barrier may comprise a container, wherein the container further comprises a void for receiving the SNF.

Alternatively the thin barrier may constitute a thin open ended container having a liquid or gaseous coolant contained inside, above, and/or below the thin open ended container configured to substantially minimize the attenuation of gamma rays produced by the SNF in the length of the open ended container between the SNF and an external area containing materials meant to be irradiated while preventing the radioisotopes that are creating the gamma rays from escaping into the external area containing materials meant to be irradiated.

The thermally conductive element may penetrate through a shielded transport container in order to remove heat from the SNF during transportation of the SNF.

The SNF storage facility may include a top level, an irradiation room level, and a bottom level, and a plurality of spent nuclear fuel (SNF) bearing containers. The SNF bearing containers are configured to contain SNF. Between the different levels of the SNF storage facility aligned penetrations are formed such that the SNF bearing containers may be maneuvered between the various levels. The SNF storage facility is further comprised of a plurality of thermal conduction elements in one embodiment of the present invention where at least one of the plurality of thermal conduction elements would be in thermal contact with at least one SNF bearing container such that at least one SNF bearing container and at least one thermal conduction element may be maneuvered as a single unit through the levels of the SNF storage facility. At least one of the thermally conductive elements is sized sufficiently in length to traverse the distance between the top level of the SNF storage facility and the bottom level of the SNF storage facility such that a substantially highly thermally conductive path from the SNF bearing container to the top level of the SNF storage facility is formed. The thermally conductive elements are visibly distinct from the SNF bearing container such that visible indication is given to workers in the irradiation room level of the SNF storage facility as to whether the SNF bearing container is still present at the irradiation room level of the SNF storage facility. The thermally conductive element is in thermal contact with an SNF bearing container, and the thermally conductive element protrudes into the top level of the SNF storage facility while the SNF bearing container is located within the irradiation room level of the SNF storage facility such that the change in the length of the thermal conduction element that is protruding through the top level of the SNF storage facility gives a visible indication of the location of the SNF bearing container within the SNF storage facility.

The plurality of SNF bearing containers may contain differing amounts of radiation being emitted by each of them and as such may be arranged in the SNF storage facility such that radiation fields of varying intensity and energy spectrum are created within the facility to provide different dose rate options for products depending on what portion of the irradiation room the products are carried through.

A transportation mechanism is implemented within the SNF storage facility, the transportation mechanism being configured to transport the SNF bearing containers from the irradiation room level to the bottom level of the SNF storage facility such that the radiation levels in the irradiation room level of the SNF storage facility can be substantially lowered by lowering the SNF bearing containers into the bottom level of the facility in one embodiment of the present invention. Thermal conduction elements may include a bulge configured such that as the SNF bearing container is lowered into the bottom level of the SNF storage facility the bulge collides with the area near its associated penetration between the irradiation room level and the top level of the SNF storage facility and prevents the SNF bearing container (which it is operably joined to) from being lowered any further and suspends the SNF bearing container above the bottom of the penetration in the bottom level of the SNF storage facility and prevents the SNF bearing container from colliding with the bottom of the penetration during a free fall. The bulge on the thermal conduction element may also be configured to shield gamma rays that would otherwise stream out through the top of the thermal conduction element and thereby prevent the creation of unwanted high radiation areas.

The present invention consists partly of a method of managing spent nuclear fuel, comprising the placement of spent nuclear fuel (SNF) into a plurality of SNF bearing containers, the SNF bearing containers being configured to allow the release of gamma radiation and prevent the release of the radioisotopes which produce the gamma radiation. These SNF bearing containers are placed in multiple locations within a SNF storage facility such that the SNF bearing containers produce substantially intense radiation levels inside of the SNF storage facility. The SNF bearing containers are separated by at least the distance required to prevent criticality accidents, and are separated by a sufficient distance from one another such that products may be maneuvered between the SNF bearing containers to receive a substantially uniform dose of gamma rays in a single pass through the facility.

Sufficient cooling of SNF during transportation of the SNF to the SNF storage facility may be achieved while the SNF is located inside of a shielded transport container by configuring thermal conduction elements to be in direct thermal contact with the SNF through penetrations in the shielded transport container. This enables the thermal conduction elements to form a direct thermal conduction pathway between the SNF and the environment such that heat from the SNF is dissipated to the environment without the release of radioisotopes to the environment.

The SNF bearing containers may be arranged within the SNF storage facility such that criticality accidents are prevented without the need for neutron poisons by separating the individual SNF elements far enough away from each other to create a high neutron leakage geometry such that the fission chain reaction does not become self-sustaining.

A method of coupling the SNF bearing containers to thermally conductive elements which reject heat to a heat sink enables SNF less than 20 months since discharge from a reactor to be maintained below a particular temperature threshold. Safe storage within the SNF bearing containers of SNF less than 7 days since discharge from a reactor is possible with this enabling technology.

The SNF rods or SNF assemblies may be encapsulated in the SNF bearing containers such that sufficient gamma radiation is emitted from the SNF bearing containers to enable sufficiently useful gamma ray irradiation of materials and products. The SNF rod or SNF assembly, according to one embodiment of the present invention, would be placed into an SNF bearing container. The SNF bearing container would then be filled with a fill material that may serve as a coolant or the SNF bearing container could also be filled with simply air or a vacuum. This SNF bearing container would then be sealed, and thus encapsulate the SNF. This encapsulated SNF could then be employed as a source of gamma rays within the SNF storage facility.

DETAILED DESCRIPTION OF THE PREFERRED EMBODIMENTS

Figure 1:
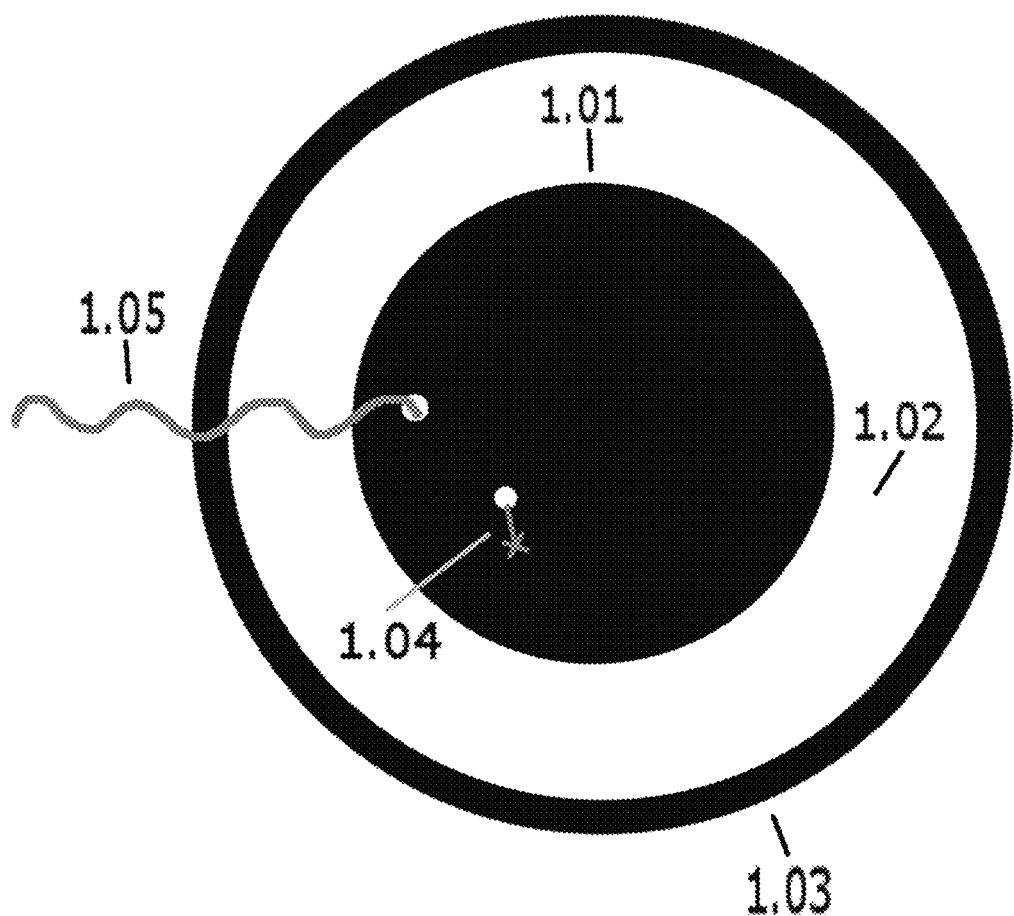
FIG. 1: Cross sectional view of an SNF bearing container and illustration of penetrating power of different forms of radiation.

Some gamma ray irradiation facility related patents have mentioned in passing that SNF could be used as an industrial gamma radiation source, for example U.S. Pat. No. 4,453,079 states "The gamma radiation sources will typically be cobalt-60 or cesium 137 and may be obtained from the waste from nuclear power plants, or the like. at a relatively low cost while using otherwise difficult to dispose of nuclear waste" but often this is referring to chemically separating Cesium 137 and other radioisotopes out of the SNF and using them as the gamma source rather than using the SNF rods and assemblies themselves as the gamma source as is suggested in the present invention. In the context of large electricity producing nuclear reactors, there has never been a satisfactory solution to allow use of SNF as a gamma radiation source in an efficient, relatively low cost, and safe manner. It has always been assumed that the extra effort of getting the SNF into an irradiation facility would not be economical because of perceived obstacles to safe storage of the SNF. There has also been uncertainty concerning the amount of gamma radiation that could truly be harvested from the SNF, ie that there would not be enough gamma radiation to make the sale of gamma rays worth the costs of harvesting them. There also have historically been fears that neutrons and other forms of high energy radiation would ruin any products you were trying to treat with the gamma rays. There have also historically been concerns that one would have to wait at least a decade to let the neutron emission levels in the SNF decay away before the gamma rays could be usefully harvested, and also that one would have to wait at least a decade for the thermal heat loads generated by the SNF to decay away such that the SNF could be safely cooled during harvesting of the gamma rays. There have also historically been concerns that the risk of criticality accidents associated with SNF would prevent the safe use of SNF in gamma irradiation facilities. The present invention embodies a safe way of storing the SNF in thin containers that would not overly absorb the gamma radiation associated with the SNF and hence allow substantial amounts of gamma rays to be harvestable. The present inventor was able to determine that neutron and other exotic high energy radiation levels in younger SNF were too low to degrade the majority of industrial products being treated with gamma rays. The present invention embodies the design of a system that avoids criticality concerns while dissipating the high heat loads from freshly discharged SNF during storage which is a substantial advancement because freshly discharged (young) SNF emits much greater amounts of gamma radiation than 10 year old SNF which means greater revenue streams from the sale of gamma rays are possible. The present inventor was able to calculate the amount of gamma radiation escaping the SNF bearing containers versus how much was being attenuated in order to show that it is highly economical and practical to use SNF as a gamma radiation source as an alternative to Cobalt-60 or Cesium 137 sources. The present inventor was able to determine that generating a revenue by selling the gamma radiation creates a scenario where the SNF storage scheme described in this patent is a highly safe, economical, and practical alternative to conventional SNF storage techniques such as dry cask storage and spent fuel pool storage.

The way in which the products are passed through the irradiation room and the prospect of gamma radiation being used for commercial applications is similar to that described in previous irradiation facility patents such as U.S. Pat. No. 6,215,847. However the concept of having several long rows of different SNF bearing containers that emit varying gamma radiation sources based on their age and utilizing independent conveyor systems carrying different products through different dose rate areas of the irradiation room to allow operational flexibility is a unique and novel feature. This allows uniform dose of the products and avoids complicated rerouting of the products via the conveyor system seen in typical irradiator designs. Because typical irradiators only have one centrally located rack of radiation sources where all of their gamma radiation radiates out from, a product going by the source only receives dose on one side and the other side of the package receives less dose and so the package must pass by the source again with the other side of it now facing the source to create a uniform dose overall. But since the conveyor system described in certain embodiments of this invention passes between multiple gamma radiation sources the package is receiving a relatively uniform dose at all times.

Previous efforts have been made to use thermally conductive elements in SNF storage but these elements transferred heat from the SNF to structural/low thermal conductivity concrete and then relied on this concrete to release heat to the local air/atmosphere as described in U.S. Pat. No. 3,667,540. However the use of thermal conduction elements to create a direct heat path through a highly conductive material to the air/outside environment is unique, especially in the context of handling much younger and thermally hotter SNF than current nuclear power industry standards.

Typical examples of dry storage technologies are described in U.S. Pat. No. 5,438,597, U.S. Pat. No. 8,351,562, and U.S. Pat. No. 4,800,062. All of these technologies focus on shielding the gamma radiation rather than letting it escape to be used for productive purposes. They also all rely on aged SNF that is not producing the substantially greater/higher heat loads associated with freshly discharged SNF. They also all rely on neutron poisons and other complicated measures to prevent criticality from occurring whereas the present invention relies on a high neutron leakage geometry to avoid creating a self-sustaining critical chain reaction process. This high neutron leakage geometry is created by spreading the SNF out rather than bringing the SNF elements in close proximity to each other. This also helps dissipate heat and is a substantial design philosophy difference when compared to the status quo techniques described in the prior art.

The conventional wisdom in the operation of a nuclear waste storage facility has been to place as much material around the SNF as substantially possible to prevent the gamma radiation from escaping so as not to harm humans that may be nearby, and to arrange the SNF as close together as possible to substantially minimize the amount of space required to store the SNF and hence save costs. The present invention takes the opposite approach by substantially minimizing the amount of fill material in the SNF bearing containers (substantially minimizing the shielding) and spreading the SNF bearing containers out across a room. In this way the gamma rays can escape and be used for a practical application, criticality safety concerns are reduced since the nuclear fission chain reaction substantially cannot be sustained when the SNF is not in close proximity to each other, and decay heat removal concerns are substantially minimized because the SNF has more space to dissipate its heat.

Previous to this invention there has been no strong commercial incentive to transfer young (0-4 years since discharge from reactor) SNF out of SNF pools located at nuclear power plants and into dry storage. This is illustrated by the common practice of storing SNF in pools as long as possible and then as a last resort nuclear power plants will implement dry storage technology. With the present invention the sooner a nuclear power plant's SNF gets placed into the SNF storage facility, the stronger its gamma source will be (because the gamma source decays away with time) and a stronger gamma source means greater revenue as the productive capacity of the irradiation room within the SNF storage facility is increased. Note that the present invention is not limited to using young SNF and SNF that has been discharged from a reactor over 80 years ago would still be usable as a gamma source.

After Fukushima there has been a public outcry to get SNF out of vulnerable SNF pools, which could leak out their water inventory and release SNF into the environment. Several political activist groups are pushing to have the SNF placed into some sort of dry storage technology. The present invention, in the majority of its embodiments, is a dry storage technology that has the advantage of being able to accept younger SNF. This creates the possibility of accelerating the removal of SNF from SNF pools since current traditional dry storage technologies can not be implemented until the SNF is several years old and the heat emitted from the SNF has decreased to a level that is manageable within the context of traditional dry cask storage technologies.

In the past the creation of gamma ray emitting encapsulated radioactive isotopes for the purpose of using them in irradiation facilities has been an intrusive process that requires several steps and introduces foreign materials into nuclear reactors. Because of this many nuclear power plants do not find it economically favorable to produce encapsulated radioactive isotopes which has led to a limited global supply. The present invention is unique in that the nuclear reactors fuel itself becomes the radioactive gamma ray source after an analogous encapsulation process. Furthermore the present invention allows nuclear reactors that have previously not had the financial incentive or technical ability to create radioisotopes for industrial applications to have an un-intrusive means of recovering value from their spent nuclear fuel by selling the gamma radiation being emitted from it while at the same time providing a novel storage location for their spent nuclear fuel. The present invention does not introduce any foreign "target" material into the reactor or create any obstacles to operating the nuclear reactor for the purposes of generating electricity. The present invention offers nuclear power plant owners a new option to recover value from their spent nuclear fuel by harvesting gamma rays that otherwise go wasted while transforming the SNF, which is generally considered a liability, into an asset.

Referring now to FIG. 1, there is illustrated one embodiment of an SNF bearing container (1.03), including SNF (1.01), and a fill material (1.02). The SNF bearing container is configured to prevent fission products, alpha radiation, and beta radiation (1.04) from contaminating the outside environment by selection of particular material(s) and dimensions. Fission products, alpha radiation, and beta radiation can not travel far through material before transferring all of their energy to their surrounding due to the physics of how these particles interact with matter. The particular material(s) and dimensions of the SNF bearing container will cause fission products, alpha radiation, and beta radiation (1.04) to transfer all of their energy to their surroundings before coming substantially close to escaping the SNF bearing container. Gamma rays (1.05) are able to penetrate through matter more easily and can therefore still escape the SNF bearing containers and transfer portions of their energy into items located outside of the SNF bearing container for the purposes of treating said outside items with gamma radiation in commercial applications. The less matter the gamma rays have to travel through in the SNF bearing container, then the more gamma rays that can escape and be sold in commercial applications. Therefore less dense materials, materials that contain fewer protons [low z], and less material are all desirable for the sake of increasing the amount of gamma rays that can be harvested from the SNF. However thicker and stronger materials are also desirable for the sake of making the SNF bearing container less fragile during accident scenarios. An appropriate selection of materials and dimensions results in an SNF bearing container exhibiting sufficient strength and durability in combination with properties allowing a sufficient percentage of gamma rays to pass through the materials when utilized to store SNF. The thin SNF bearing container, or thin barrier between the SNF and the products being irradiated by the gamma rays, may range from 0.0001 cm to 15 cm thick. Although the SNF bearing container (1.03) is illustrated as being cylindrical in shape, the invention is not so limited. The SNF bearing container (1.03) may comprise other shapes including cubic, oval, or any shape that would be capable of forming an interior void for storing SNF.

Figure 2A:
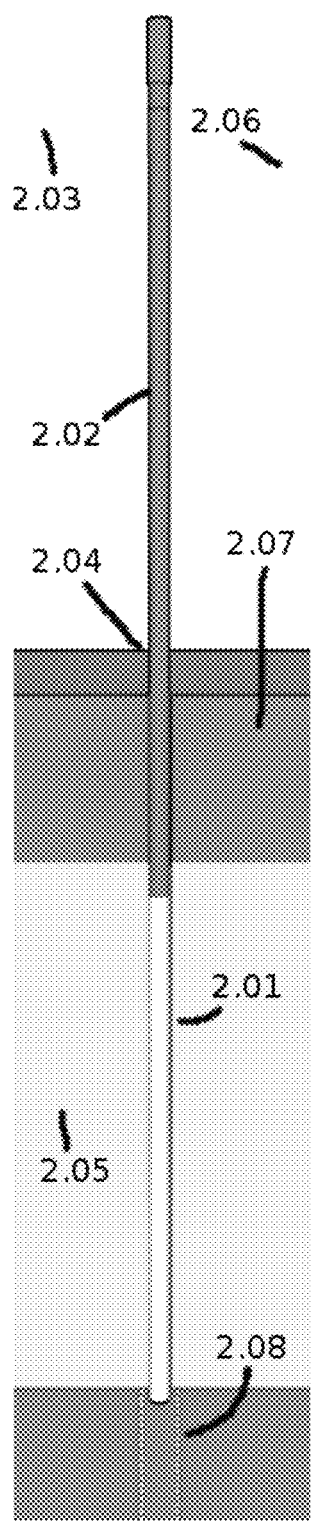
FIGS. 2A-B: Illustration of heat dissipation through the SNF bearing container to the thermal conduction element which carries heat out of the irradiation room and into the top level of the SNF storage facility.
Figure 2B:
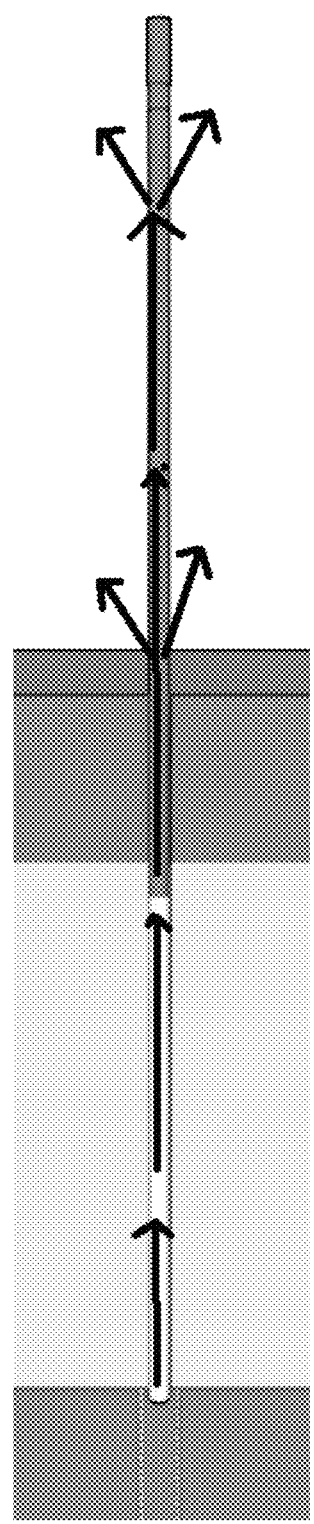

The present invention is also directed toward the issue of keeping the SNF below a particular temperature threshold by creating at least one thermally conductive pathway that allows heat to travel away from the SNF. Referring now to FIG. 2A, there is illustrated a thermal conduction element (2.02), which may be thermally coupled with the SNF bearing container (1.03) illustrated in FIG. 1 and also illustrated in FIG. 2 as 2.01. For example, in one embodiment, the thermal conduction element (2.02) may be coupled to an SNF bearing container (2.01), and this creates a path for thermal conduction to carry the heat generated by the SNF out into the top room (2.06) towards an ultimate heat sink (2.03), as just one example as illustrated in FIG. 2B where the path of heat is represented by arrows. The bottom level of the SNF storage facility and its borehole (2.08) which allows for the storage of the SNF bearing container in the bottom level of the SNF storage facility can also be seen in FIGS. 2A and 2B. The location where the thermal conduction element makes contact (2.04) with the roof (2.07) of the irradiation room (2.05) during normal operation can be composed of a highly thermally conductive material to assist in heat rejection out of the facility. The SNF storage facility is thus able to sufficiently cool young SNF during storage in a completely passive manner in this embodiment of the present invention.

To this end, the material composition of the thermal conduction element, SNF bearing container, and fill material are all chosen to improve the effectiveness of thermal conductivity and hence heat rejection to the ultimate heat sink. Aluminum is a suitable material for the container and thermal conduction element but the scope of this invention is not limited in this respect. For example borated aluminum, plastic, steel, copper, and other materials having suitable thermal conductivity properties may be incorporated and remain within the scope of the invention. Solid resin, epoxy, nylon, polyethylene, etc would be a suitable fill material (1.02) however it would not pass beyond the scope of the invention to use another material such as water, air, Helium, glass, a vacuum, etc that transfers enough heat away from the SNF without prohibitively shielding too many of the gamma rays. Resin, or a similarly hard curing material, has the advantage of encasing the SNF and acting as another barrier to fission product release to the environment in case of an SNF bearing container (1.03) rupture accident. It is desirable that the fill material and SNF bearing container material be suitably transparent to gamma rays by being relatively low in density, thickness, and number of protons.

Figure 3A:
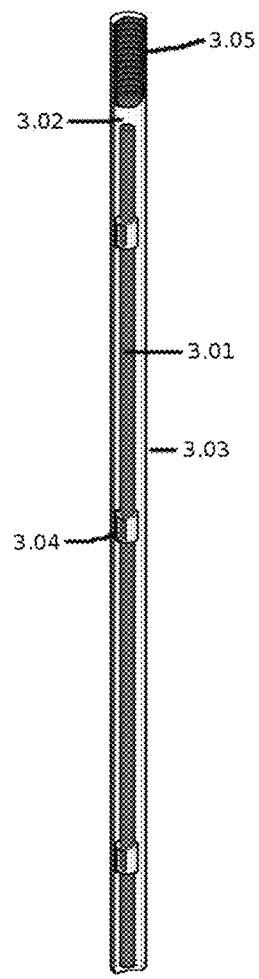
FIGS. 3A-C: Cutaway views of SNF bearing containers according to different embodiments of the invention
Figure 3B:
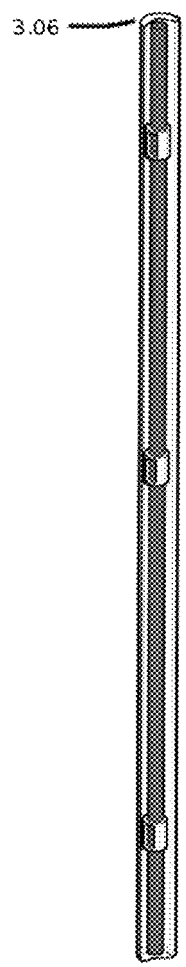
Figure 3C:
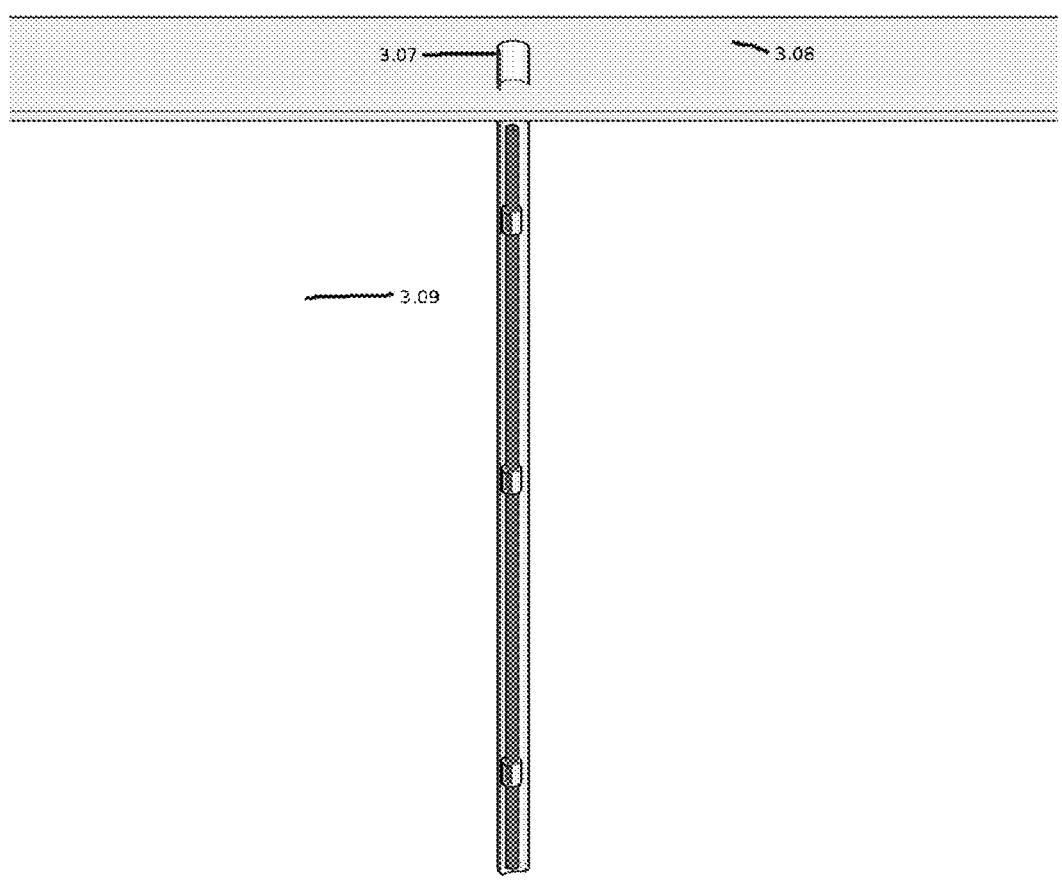

Referring now to FIG. 3, it can be seen that the SNF (3.01) rests inside of the SNF bearing container (3.03) while surrounded by fill material (3.02). In one embodiment the SNF bearing container seen in FIG. 3 (3.03) & FIG. 2 (2.01) contains rigid supports (3.04) that substantially mimic the spacer grids or support plates inside of conventional nuclear fuel assemblies and nuclear reactor cores. These rigid supports guide the SNF into the container during loading and provide support to minimize seismic damage or fall damage during an earthquake or fuel drop accident. The top of the SNF bearing container may contain threading (3.05) or some other joining mechanism that is meant to facilitate the coupling of the thermal conduction element to the SNF bearing container. In another embodiment a welding process can be used to seal the top of the SNF bearing container should the threading or other joining mechanism not create an airtight seal. Referring to FIG. 3B, in yet another embodiment the SNF bearing container can simply be closed off or welded at the top (3.06) and not contain any joining mechanism. Referring to FIG. 3C, in yet another embodiment the SNF bearing container can be open ended (3.07) such that liquid or gaseous coolant that provides contamination controls and cooling mechanisms can be implemented inside, above, and/or below the thin open ended container in an area (3.08) segregated from the external area containing materials meant to be irradiated (3.09) such that the attenuation of gamma rays is substantially minimized across the length of the SNF and the external area containing materials meant to be irradiated while preventing the radioisotopes that are creating the gamma rays from escaping into the external area which contains materials meant to be irradiated.

Figure 4A:
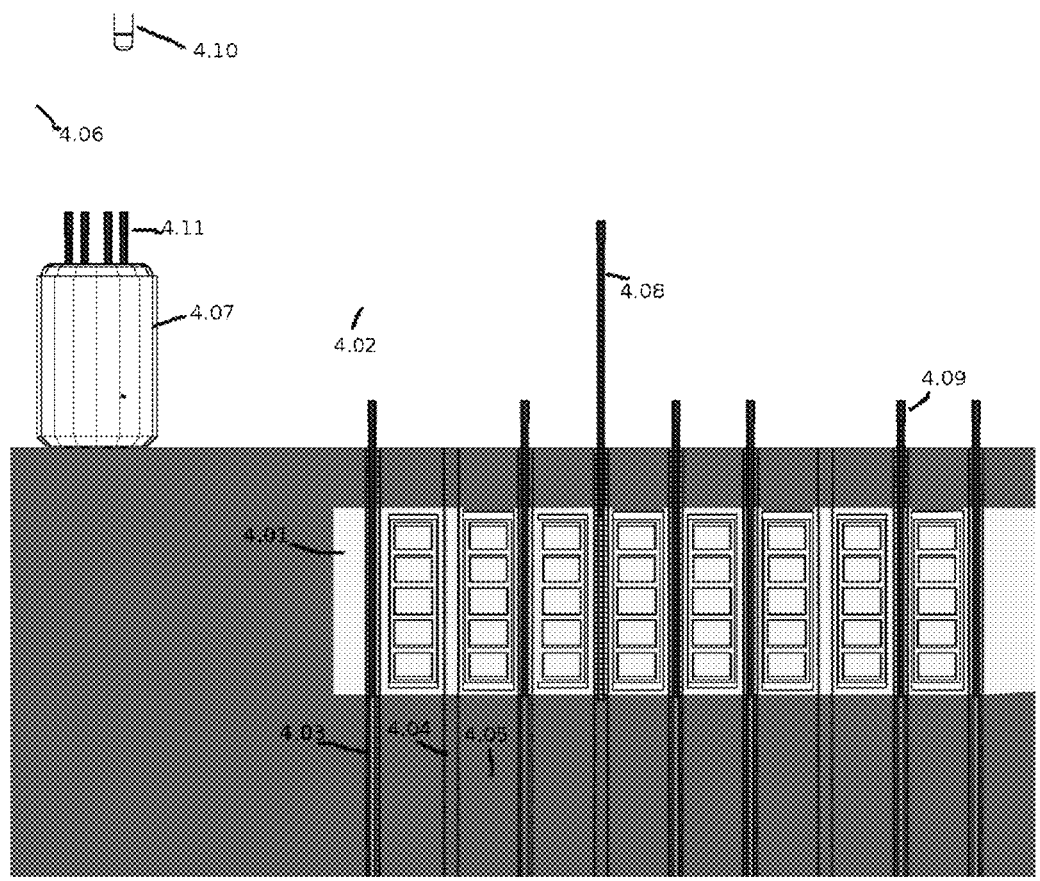
FIGS. 4A-J: Cross sectional view of the SNF storage facility and a rough illustration of how SNF bearing containers are loaded into the SNF storage facility according to one embodiment of the invention.

Referring now to FIG. 4A, the purpose of different sections of the SNF storage facility can be seen. The irradiation room (4.01) is located below the top level (4.02) of the SNF storage facility. SNF bearing containers (4.03) can be lowered into boreholes (4.04) in the foundation of the bottom level (4.05) of the facility such that radiation levels in the irradiation room can be lowered when desired. A SNF transfer bay area (4.06) is located at the facility for the purpose of allowing SNF to be brought into the facility via a shielded transport container (4.07) which may be carried by a lifting vehicle. The thermal conduction elements (4.08) remain in the top level of the SNF storage facility during normal operation and the SNF bearing container, which is attached to the thermal conduction element, is inside of the irradiation room during normal operation. In order to lower the radiation levels in the irradiation room the SNF bearing containers may be lowered into the foundational material of the floor of the irradiation room, which can be termed the lower level of the SNF storage facility or boreholes. The thermal conduction element may be sized such that even when the SNF container has been lowered into a borehole a portion of the thermal conduction element is still exposed (4.09) to the top level of the SNF storage facility which allows heat to still be rejected to the top level of the facility. Also, vents can be strategically placed to intake cold air and release warm air to assist in the convective heat transfer occurring inside of the SNF storage facility in order to cool the irradiation room.

Figure 4B:
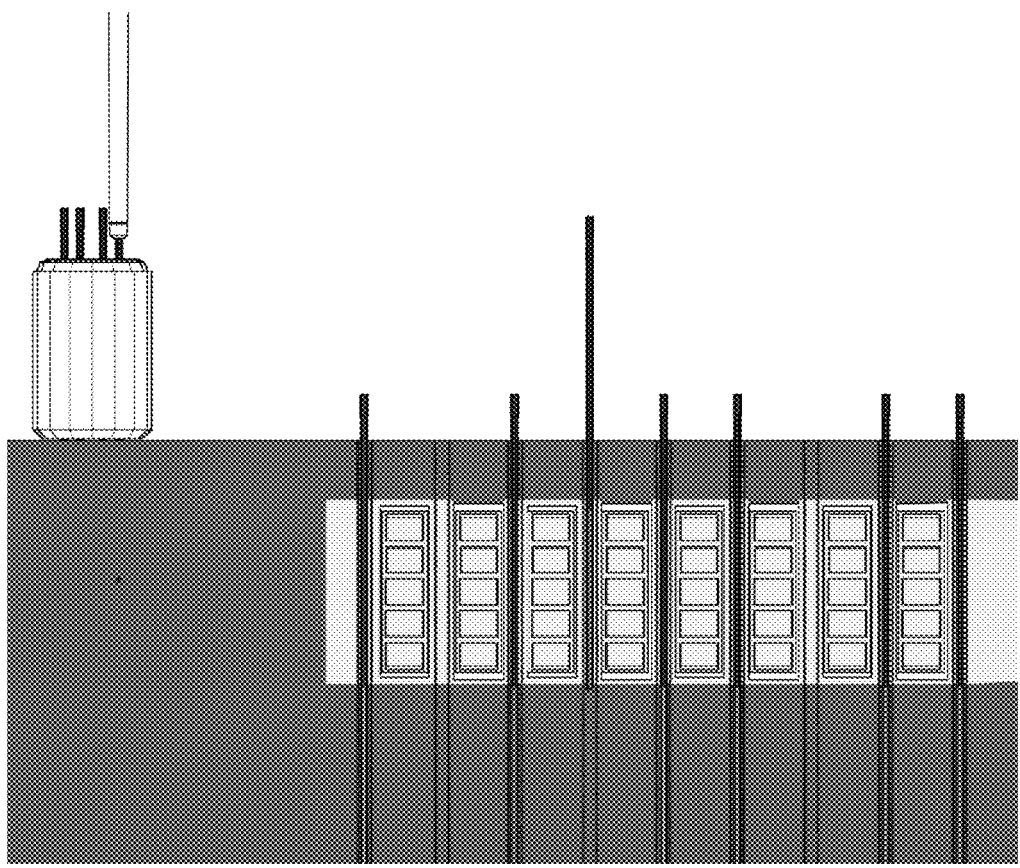
Figure 4C:
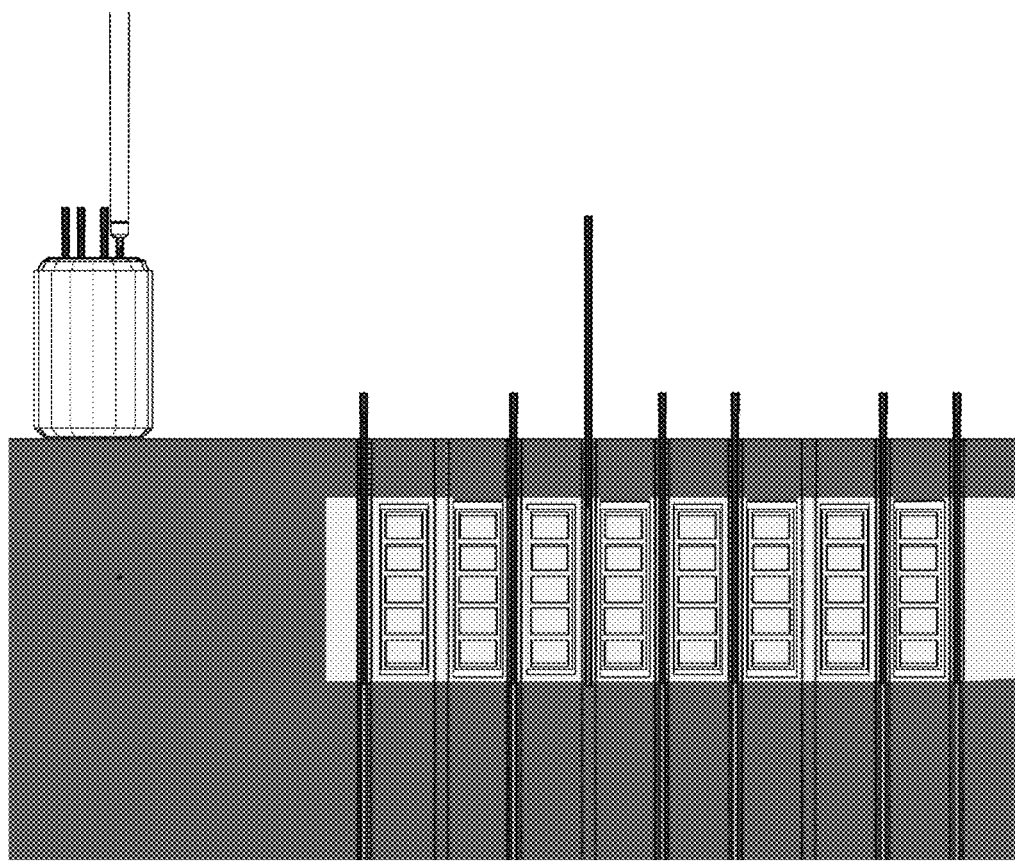
Figure 4D:
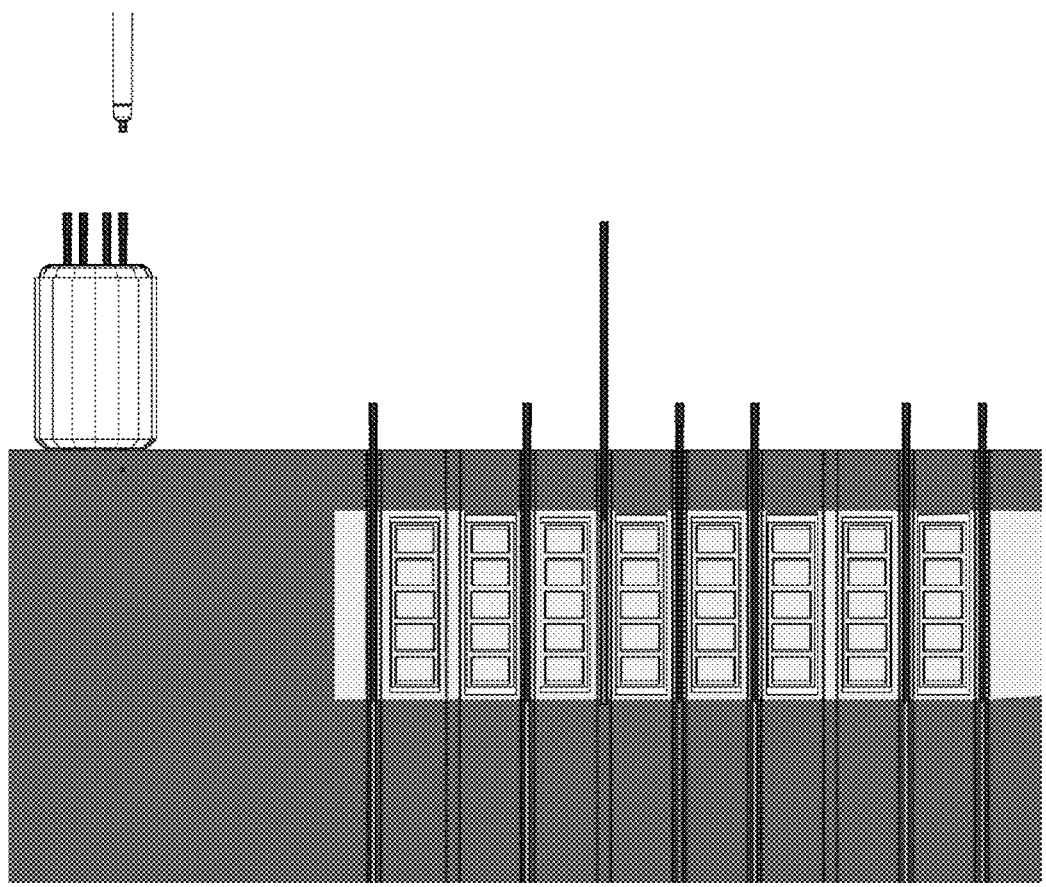
Figure 4E:
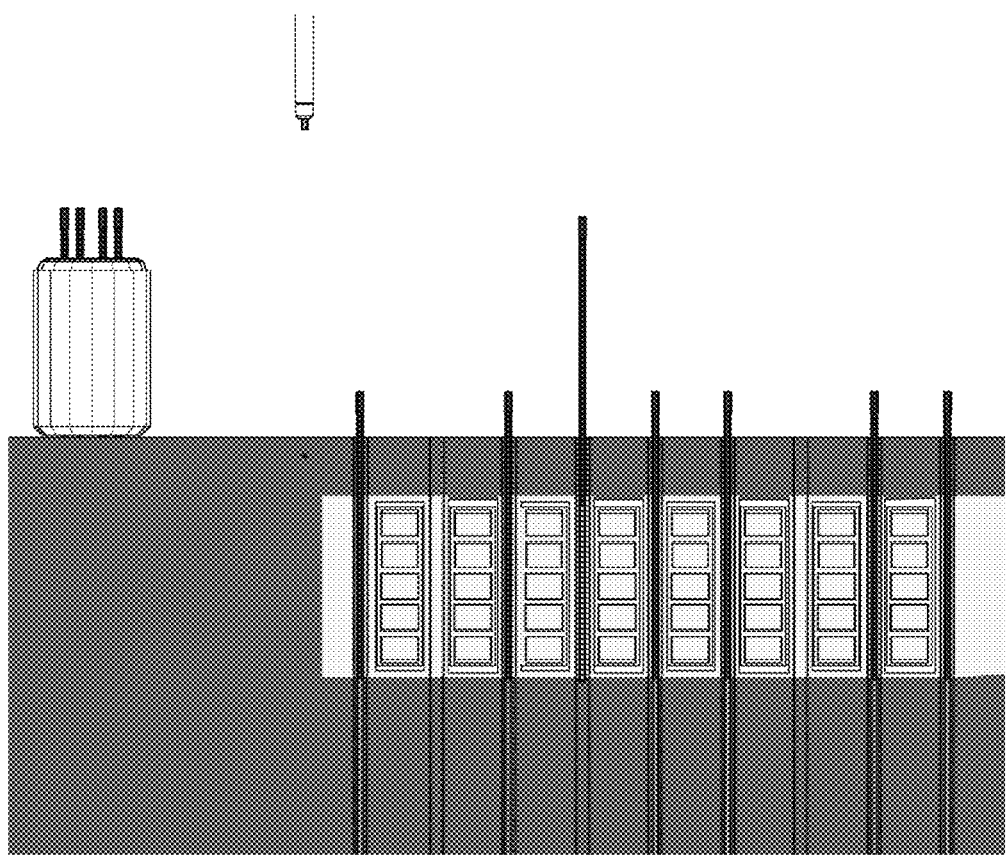
Figure 4F:
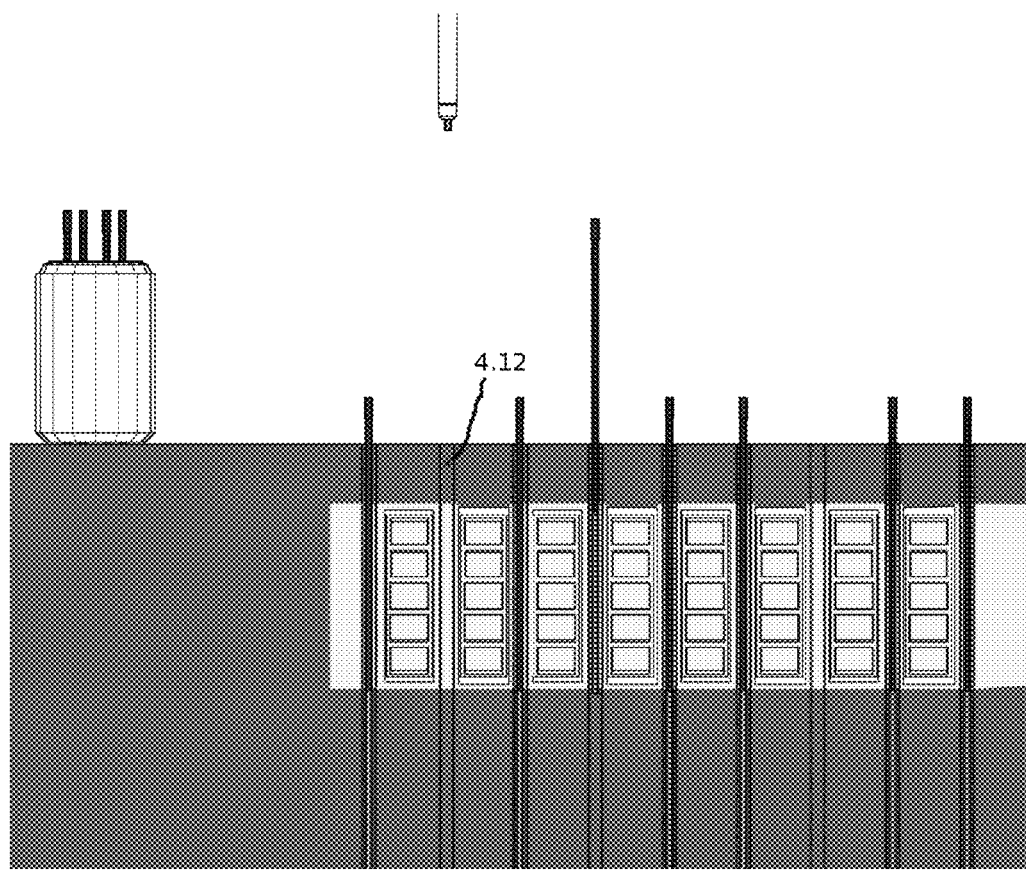
Figure 4G:
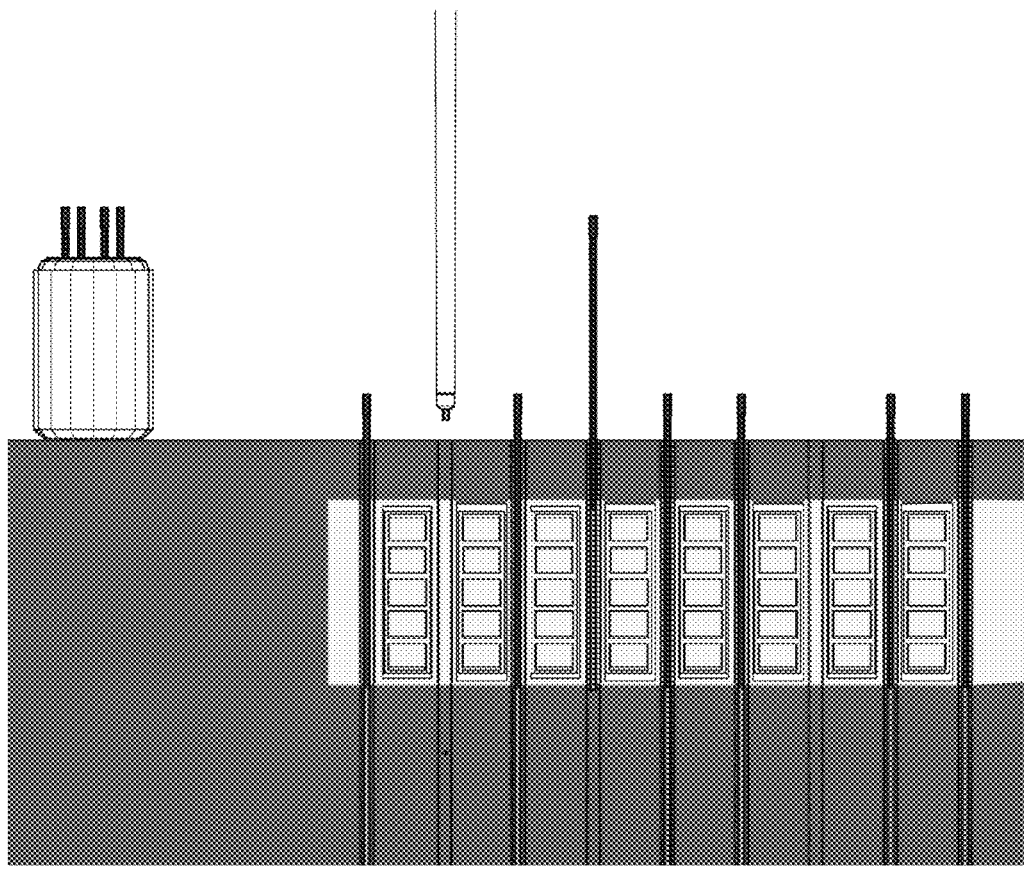
Figure 4H:
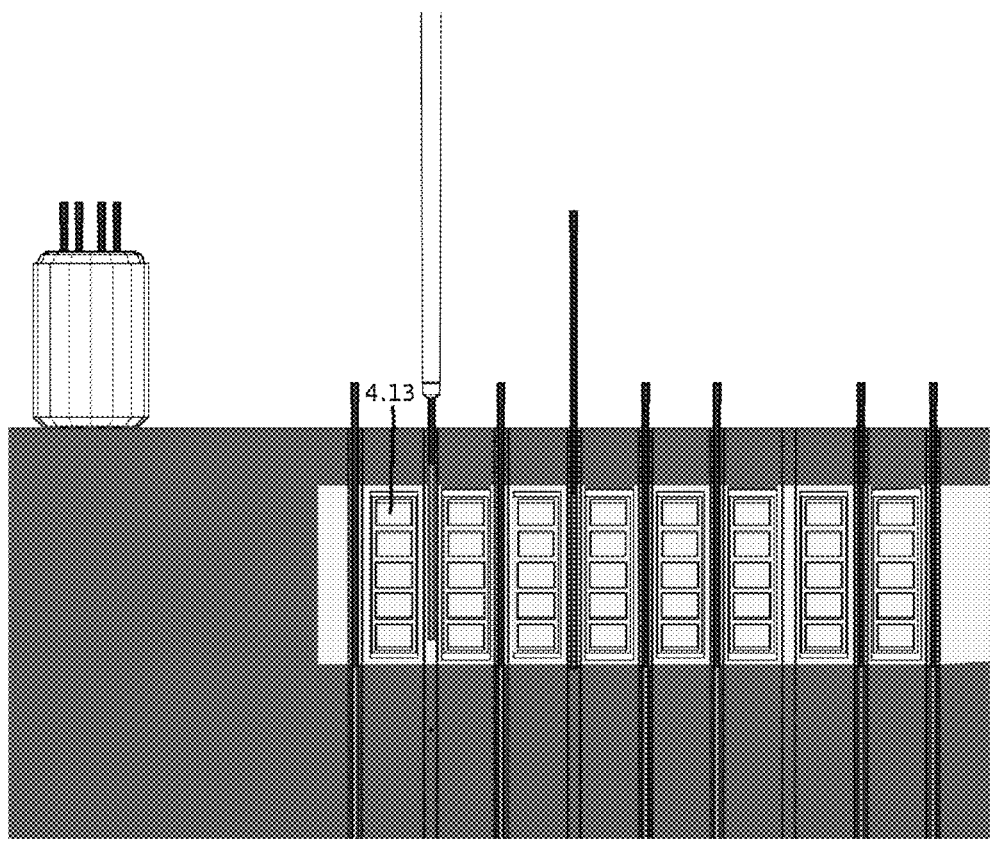
Figure 4I:
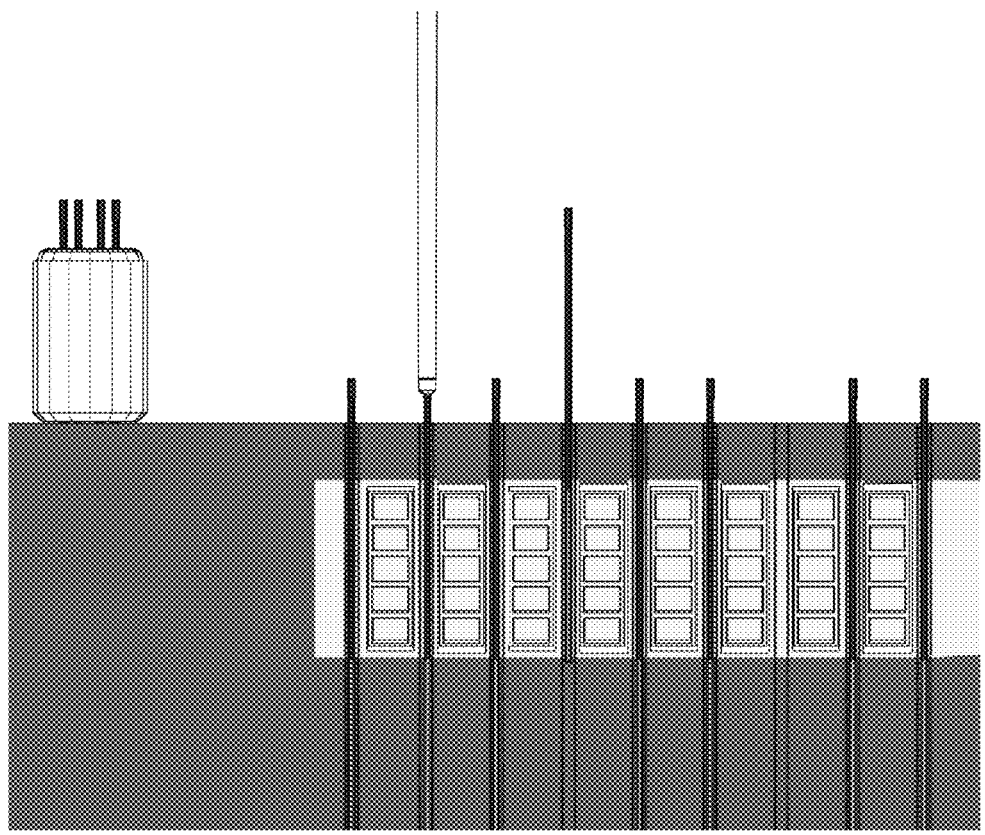
Figure 4J:
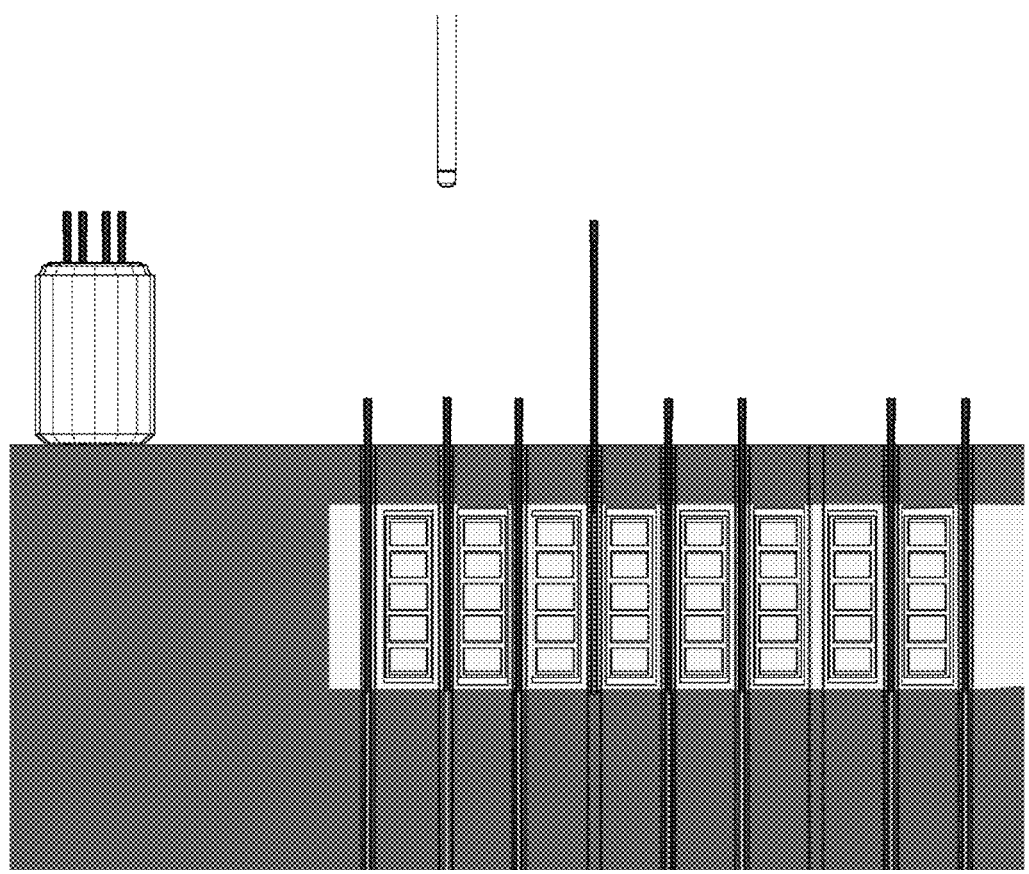

Referring to FIG. 4A through FIG. 4J the loading process of SNF bearing containers into the SNF storage facility is illustrated according to one embodiment of the invention. In FIG. 4A an overhead crane system (4.10) can maneuver into the fuel transfer bay and become aligned over SNF bearing containers and their associated thermal conduction elements (4.11) that are located inside of a shielded transport container. In FIG. 4B the overhead crane connects with the thermal conduction element. In FIG. 4C the overhead crane further secures its connection with the SNF bearing container. In FIG. 4D the overhead crane lifts the SNF bearing container into the air. In FIG. 4E the overhead crane begins to move from the fuel transfer bay to the top level of the facility. In FIG. 4F the overhead crane positions itself over a penetration (4.12) in the roof of the irradiation facility that is meant to accept the SNF bearing container. In FIG. 4G the overhead crane lowers down to the penetration in the roof of the irradiation facility that is meant to accept the SNF bearing container. In FIG. 4H the overhead crane lowers the SNF bearing container into the irradiation room where materials meant to be irradiated are located inside of boxes being carried by an overhead conveyor system (4.13). In FIG. 4I the overhead crane lowers the SNF bearing container into the borehole at the bottom level of the facility. In FIG. 4J the overhead crane pulls away and is ready to perform other fuel handling functions.

Figure 5A:
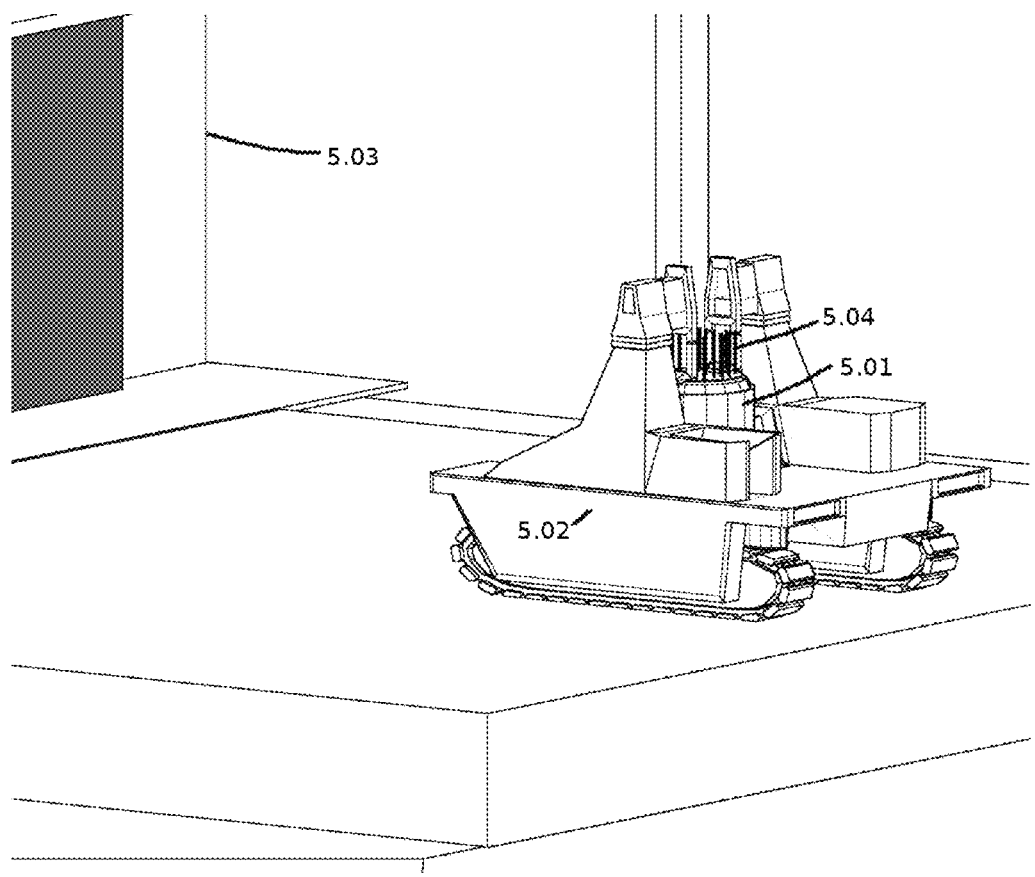
FIG. 5A-5H: Illustration of SNF bearing containers being transported to the SNF storage facility and thermal conduction elements being applied during the SNF transportation process according to one embodiment of the invention

Referring now to FIG. 5A, a shielded transport container is shown (5.01), according to one embodiment of the invention, being carried by a lifting vehicle (5.02) on its way to the SNF storage facility (5.03). The shielded transport container absorbs the gamma radiation coming from the SNF bearing containers inside of the shielded transport container and prevents workers from being exposed to high levels of radiation during transportation. The lifting vehicle is able to carry the weight of the shielded transport container that is filled with SNF bearing containers. The SNF bearing containers are lowered into the shielded transport container via small openings. These small openings can be sealed shut if there is not a full load of SNF bearing containers inside of the shielded transport container. Thermal conduction elements (5.04) that are coupled to the SNF bearing containers inside of the shielded transport container create a direct heat rejection pathway to the environment/ultimate heat sink which allows younger SNF that is generating higher heat loads to be transported to the SNF storage facility compared to traditional shielded transport containers. In other embodiments of the invention the SNF would be transferred into the SNF bearing containers at the SNF storage facility rather than being transported to the SNF storage facility already in SNF bearing containers. Any penetration in the shielded container can be sealed with a plug in the case of a penetration that is not currently occupied by an SNF bearing container to lower worker exposure to radiation.

Figure 5B:
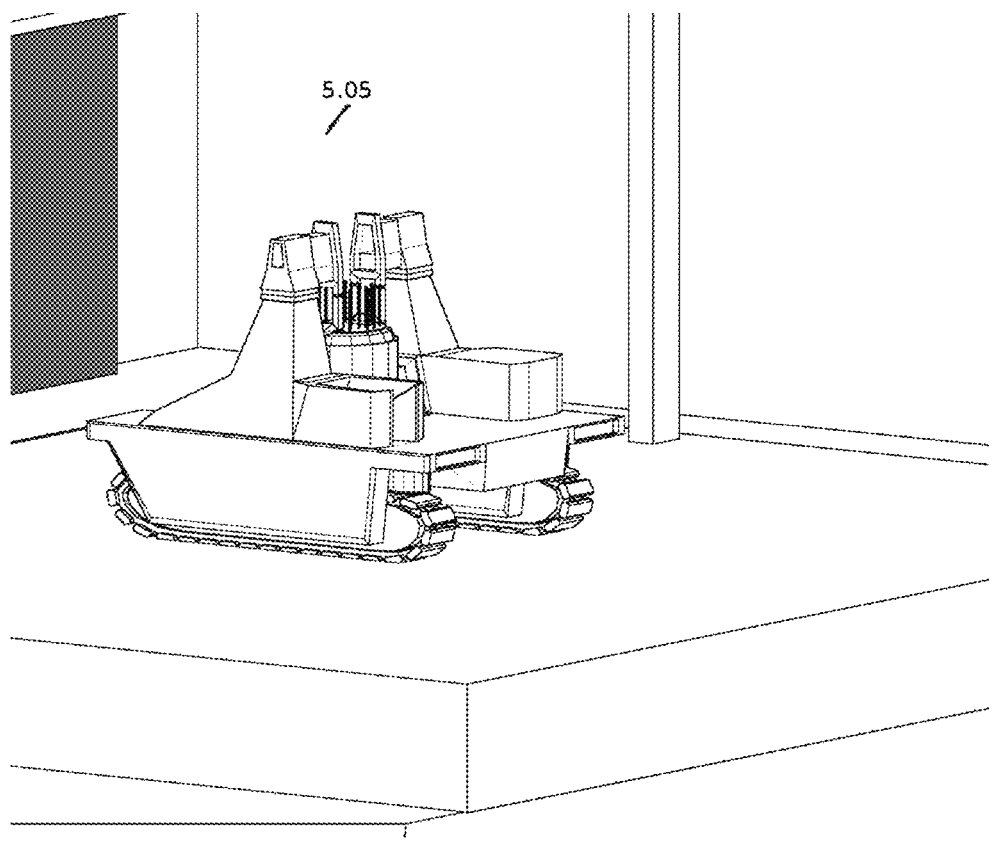
Figure 5C:
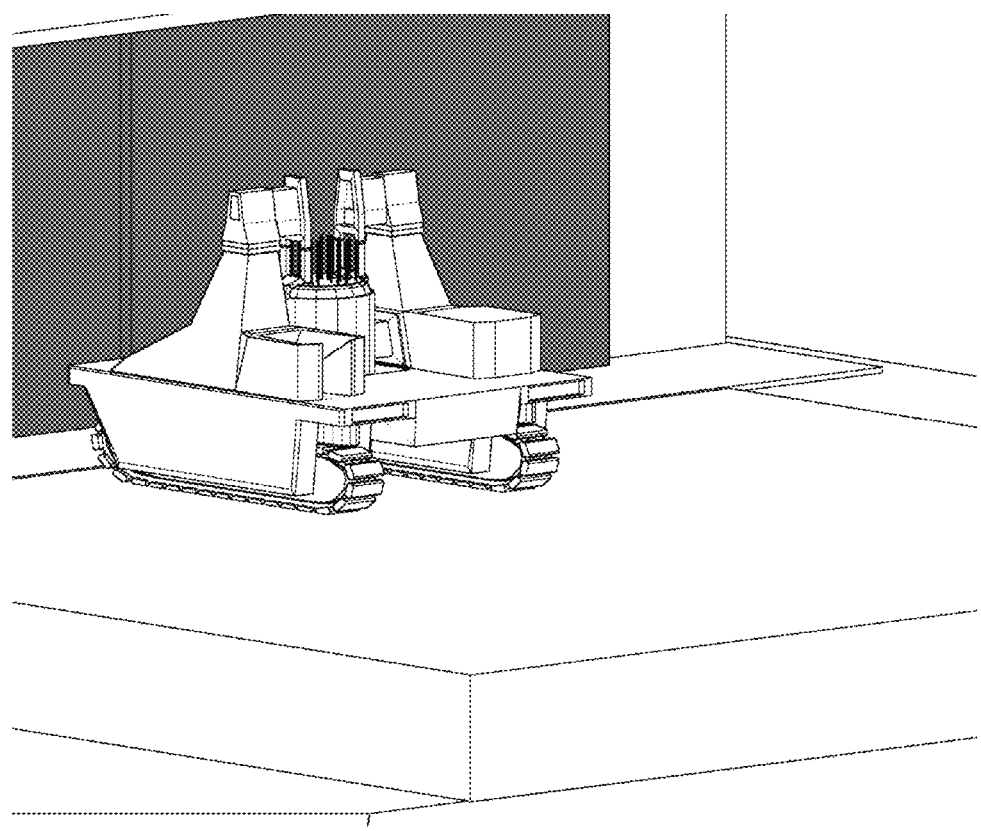
Figure 5D:
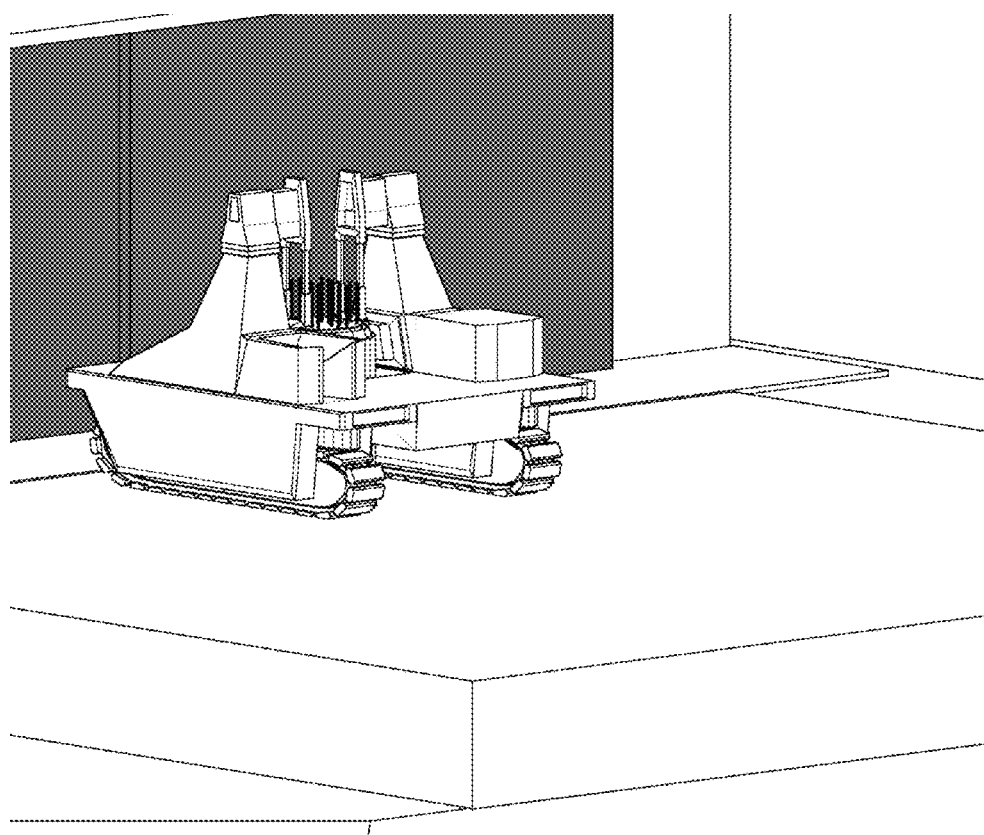
Figure 5E:
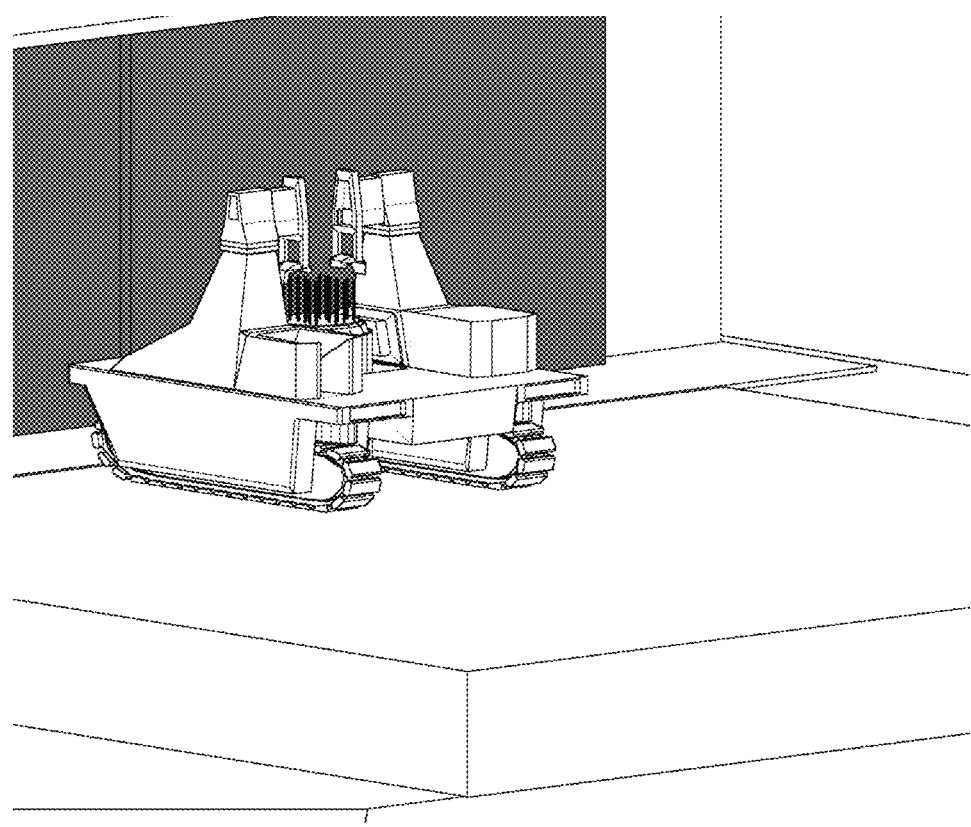
Figure 5F:
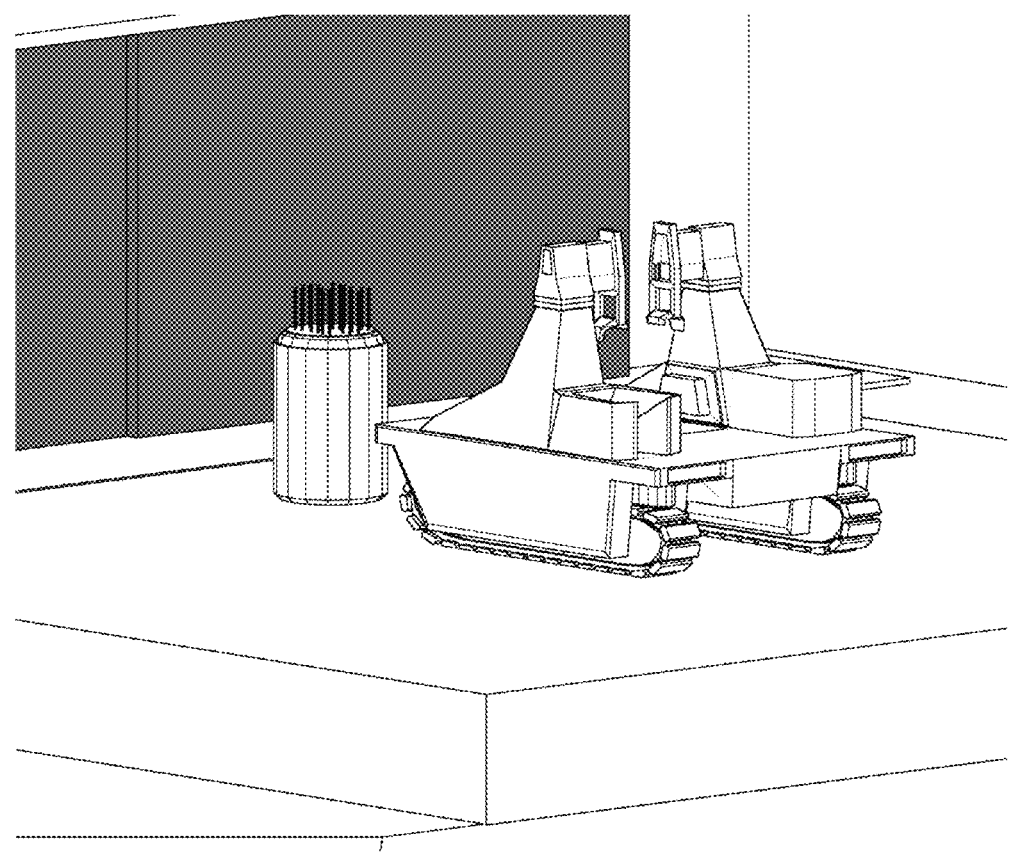
Figure 5G:
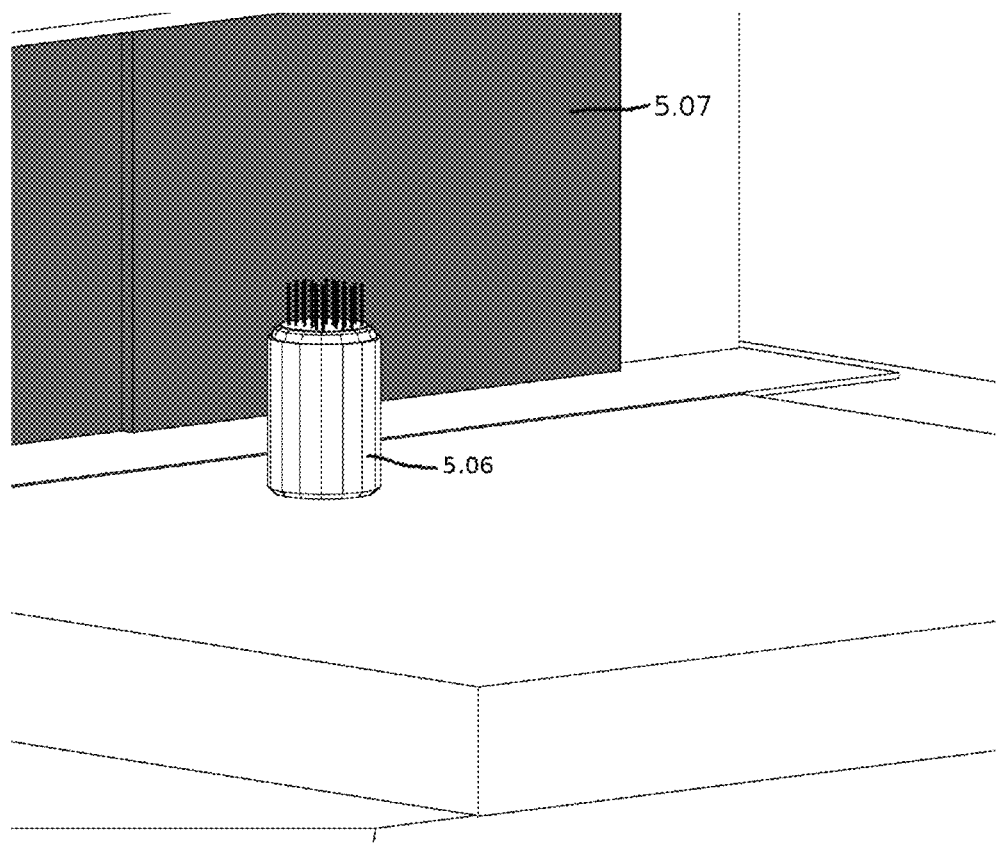
Figure 5H:
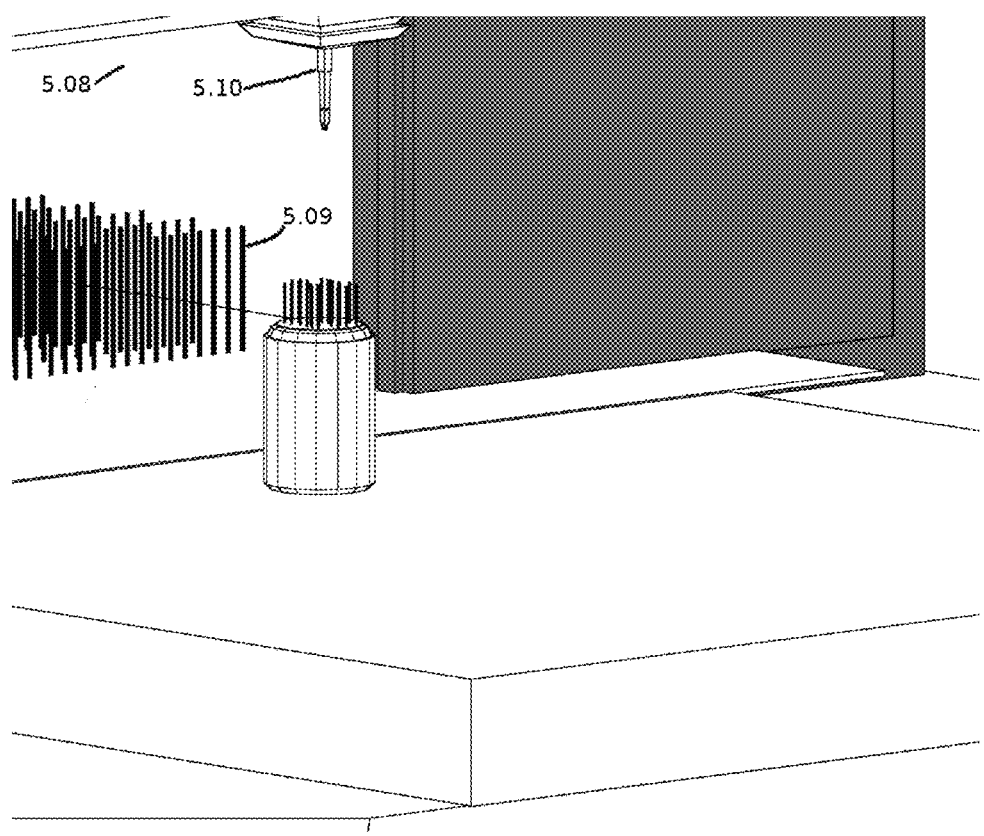

Referring now to FIG. 5B through FIG. 5H the transportation of SNF bearing containers to the SNF storage facility is illustrated according to one embodiment of the invention. In FIG. 5B the lifting vehicle is approaching the SNF storage facility and the SNF transfer bay (5.05). In FIG. 5C the lifting vehicle pulls into the SNF transfer bay. In FIG. 5D the lifting vehicle lowers the shielded transport container onto the floor of the SNF transfer bay. In FIG. 5E the lifting vehicle fully releases the shielded transport container. In FIG. 5F the lifting vehicle drives out of the SNF transfer bay. In FIG. 5G the shielded transport container (5.06) is sitting in the SNF transfer bay waiting for the hangar doors (5.07) that separate the top level of the SNF storage facility and the SNF transfer bay to open. In FIG. 5H the hangar doors have been opened to reveal the top level of the SNF storage facility (5.08), the thermal conduction elements (5.09) that are located at the top level of the SNF storage facility, and the overhead crane system (5.10) that will begin the loading sequence described in FIG. 4A through FIG. 4J.

Figure 6:
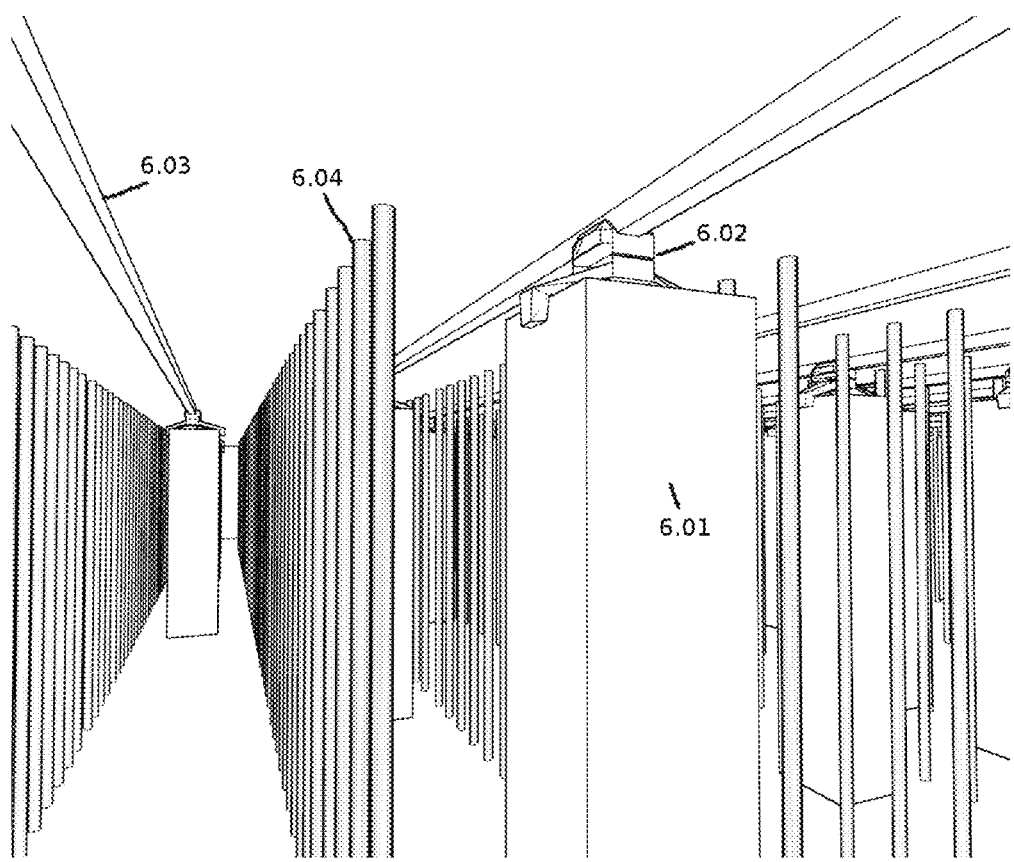
FIG. 6: Illustration of the irradiation room and the overhead conveyor system that carries products through the irradiation room according to one embodiment of the invention.

Referring now to FIG. 6, an embodiment of the present invention is shown wherein boxes full of products/materials (6.01) meant to be irradiated are transported through the irradiation room via an overhead conveyor system (6.02). The path traveled by the overhead conveyor system is rigidly restricted by the track system (6.03) seen on the roof of the irradiation room. The overhead conveyor system travels in between the rows of SNF bearing containers (6.04) such that a homogeneous dose of gamma rays is delivered to both sides of the boxes full of products simultaneously. The rows of SNF bearing containers may be spaced anywhere from 0.01 meters to 15 meters apart although roughly 1 meter apart is the preferred embodiment. The spacing between SNF bearing containers in the same row may be anywhere from 0 centimeters to an infinite distance apart in various embodiments of the present invention, although the preferred embodiment is roughly 4 centimeters of distance separating each SNF bearing container.

Figure 7:
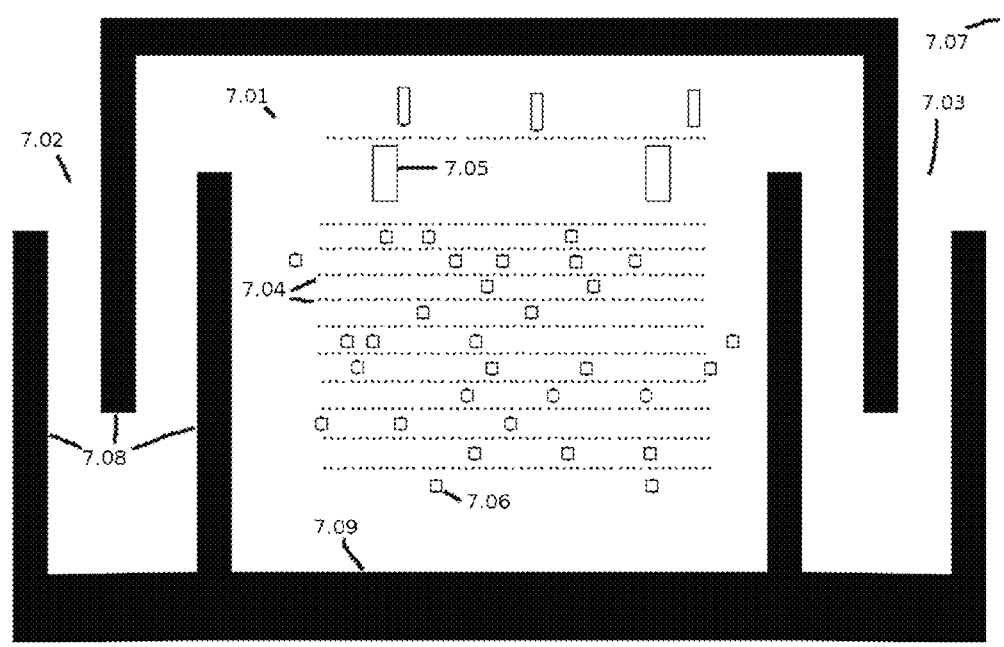
FIG. 7: Cross sectional view of the irradiation room filled with SNF bearing containers and boxes of products according to one embodiment of the invention.

Referring now to FIG. 7, a cross sectional view of the irradiation room (7.01) and the associated entrance (7.02) and exit (7.03) into and out of the irradiation room according to one embodiment of the present invention can be seen. The SNF storage facility will contain SNF of varying age and radiation intensity. The radiation levels throughout the irradiation room can be adjusted by rearranging where particular SNF bearing containers are located since each SNF fuel rod will have a different energy spectrum and intensity of gamma rays being emitted from it based on where the SNF rod was located inside of the nuclear reactor, what operational parameters were used in the nuclear reactor during a particular operating cycle, and how long it has been since the SNF was removed from the reactor, among other factors. In one embodiment all of the youngest SNF bearing containers (those with the highest gamma radiation emissions) can be located in a particular location within the irradiation room such that products which desire higher dose rates can be sent through that portion of the irradiation room and products which can effectively be treated at lower dose rates can be sent through other portions of the irradiation room. The SNF bearing containers (7.04) are spread out into rows separated by uniform distances, but to accommodate larger products (7.05) a larger distance between rows may be implemented. Independent conveyor systems allow operators the flexibility to perform dose verifications on small samples without interfering with operations of the rest of the product transportation lines in the irradiation room. It also enables different product batches to receive different doses in parallel and reduces the fraction of wasted gamma rays that deposit their energy into objects other than the products (7.06). A product processing station (7.07) adjacent to the irradiation room is used to load conveyor systems with products and to check the product packaging for security purposes via workers or an automated loading system. The conveyor system follows a guided path into and out of the irradiation room which optionally could pass through airlocks that prevent contaminated air from reaching the workers in the unlikely event of an accident. The workers are protected from the high gamma radiation levels of the irradiation room by a labyrinth (7.08) or similar shielding structure. The heavy construction materials (7.09) around the irradiation room which the SNF storage facility is composed of helps protect the SNF from natural and man-made threats while simultaneously protecting the public from the radiation emitted by the SNF.

Figure 8:
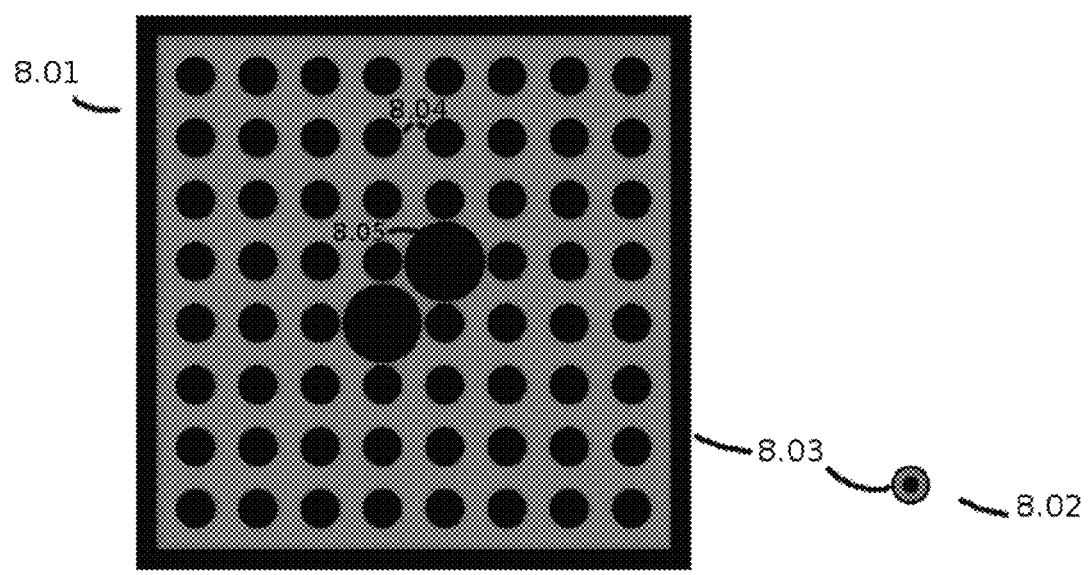
FIG. 8: Illustration of SNF stored in SNF bearing containers on an assembly basis versus on a fuel rod basis according to one embodiment of the invention

There are several different types of SNF associated with different nuclear reactor designs and the present invention can be applied to any of them, especially SNF from light water and heavy water reactors. Referring now to FIG. 8, two different forms of SNF produced from light water reactors [(SNF assembly (8.01) and SNF rod (8.02)] are shown in a cross sectional view inside of SNF bearing containers (8.03). A typical SNF assembly removed from a nuclear reactor is composed of tens to hundreds of SNF rods (8.04), instrumentation tubes (8.05), and structural supports. This constitutes a disadvantage in terms of allowing gamma rays to escape out into the irradiation room. The SNF within such an assembly is an effective gamma ray shield, such that gamma rays produced by SNF in the center of the assembly will deposit a significant portion of their energy in the surrounding SNF instead of allowing more of the gamma ray energy to escape the SNF bearing container. However, despite this issue the SNF assembly bearing container can more densely pack SNF inside of the SNF storage facility which could make it a more attractive embodiment of the present invention than the SNF rod bearing embodiment in some scenarios, particularly when the monetary value of storing SNF exceeds the monetary value of harvesting the gamma rays emitted by the SNF. Most SNF is discharged from reactors in assembly form so placing the entire assembly into a SNF bearing container eliminates the process of disassembling the fuel assembly. However, disassembling the SNF assembly and individually placing each SNF rod in its own SNF bearing container reduces SNF bearing container heat loads, reduces gamma ray shielding, reduces weight, and greatly enhances the fraction of gamma rays generated in the SNF that can ultimately deposit their energy into products in the irradiation room. When storage of SNF is the greater priority it is advantageous to place SNF into the facility on a fuel assembly basis. This allows much more of the SNF generated by a nuclear power plant to reside inside of the SNF storage facility. When stored on an individual fuel rod basis it may be more advantageous to only store a few refuelings worth of SNF at the SNF storage facility and then remove older SNF bearing containers from the facility and replace them with more freshly discharged ones due to the issue of a large volume of space being occupied by the SNF when spread out into individual fuel rods. In this manner SNF storage facility size and costs are kept substantially low but fresh SNF keeps the harvestable gamma signal attractively high.

Figure 9A:
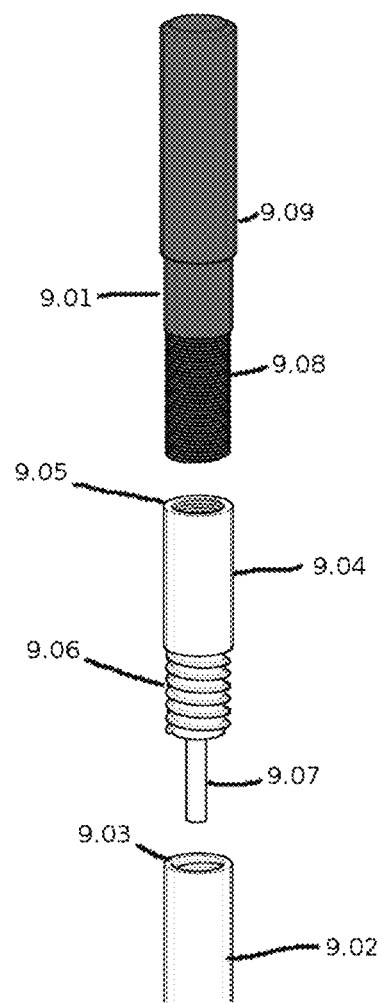
FIG. 9A-D: Illustrations of how the SNF bearing container is coupled to the thermal conduction element according to some different embodiments of the invention.
Figure 9B:

Referring now to FIG. 9A, the mechanism by which the thermal conduction element (9.01) is joined to the SNF bearing container (9.02) according to one embodiment of the invention is shown. The SNF is submerged in a fill material inside of the SNF bearing container. The bottom of the SNF bearing container is of solid closed construction and the top of the SNF bearing container has an opening (9.03) with female threading. A connection piece (9.04) with female threading on top (9.05), male threading on the bottom (9.06), and a rod (9.07) extending out of its bottom and into the fill material is used to mediate the union of the thermal conduction element and the SNF bearing container. A gap may be left between the fill material and the top of the SNF bearing container that allows thermal expansion of the fill material to occur without over pressurizing the SNF bearing container. The small gap also prevents the fill material from leaking out of the SNF bearing container during the initial loading of fill material into the SNF bearing container. The small gap reduces the thermal conduction occurring between the fill material and the connection piece but some of this loss can be recovered by the rod which extends from the bottom of the connection piece and into the fill material. The thermal conduction element (which is a solid rod, or similar shape, composed of a highly thermal conductive material, such as Aluminum or Copper) contains male threading (9.08) which couples to the female threading seen in the connection piece such that a solid union which enables thermal conduction is made between the SNF bearing container, connection piece, and thermal conduction element and the three individual parts become a single unit as seen in FIG. 9B.

Figure 9C:
Figure 9D:

As seen in FIG. 9C, in another embodiment the thermal conduction element and the SNF bearing container can be connected without the aid of a connection piece which reduces connection complexity but also reduces SNF handling flexibility during the transportation process. The advantage of using a connection piece is that different thermal conduction elements of varying lengths can be applied to the SNF bearing container between when the SNF bearing container is sitting in the irradiation room and when the SNF bearing container is being transported to the SNF storage facility. For example, shorter thermal conduction elements (As seen in FIG. 9D) may be implemented while the SNF bearing containers are in the shielded transport cask because there is a shorter distance between the SNF and the ultimate heat sink during that stage of the storage process.

Figure 11A:
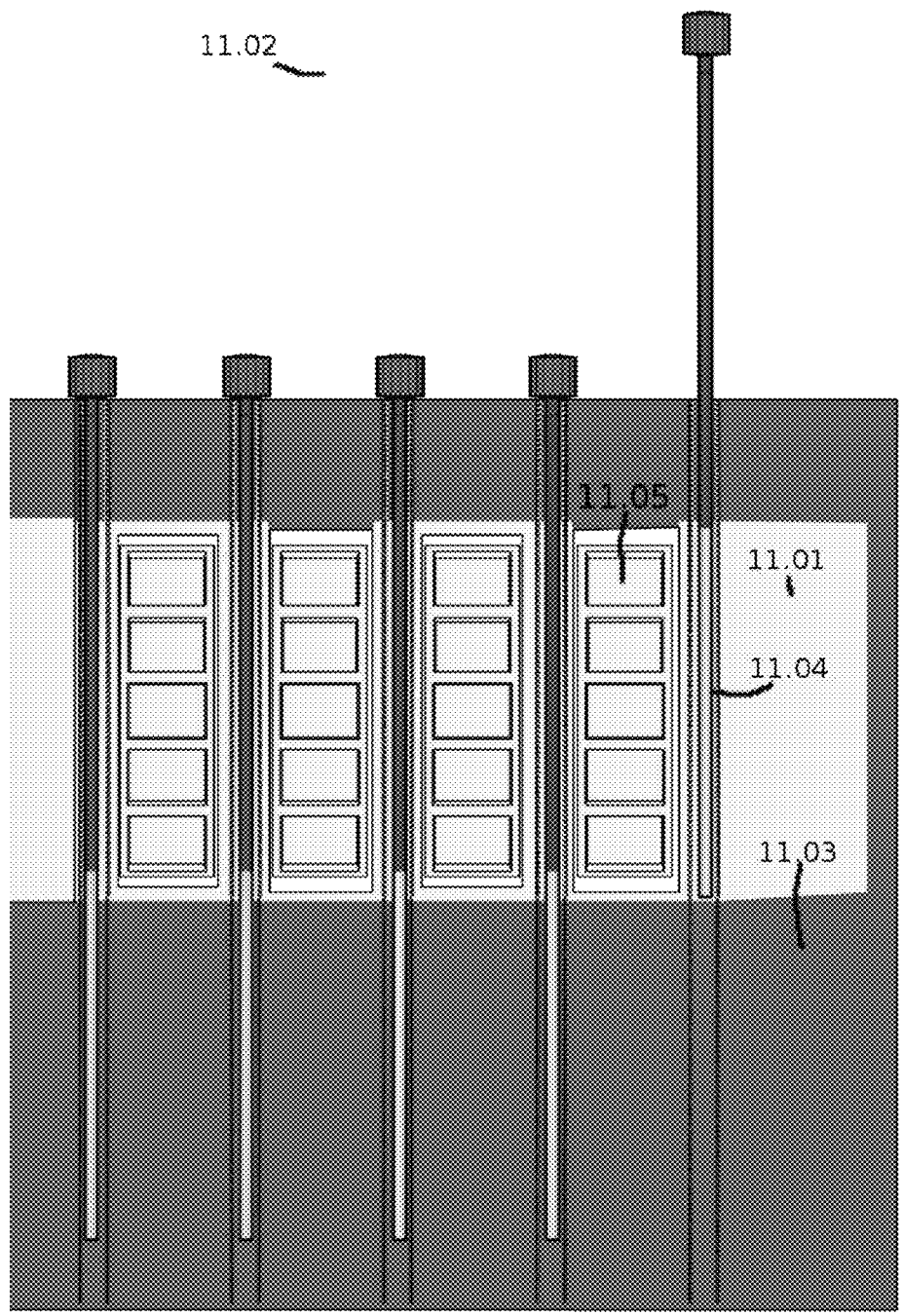
FIG. 11A-11C: Illustration of the movement of a SNF bearing container from the irradiation room level to the bottom level of the SNF storage facility according to one embodiment of the invention.
Figure 11B:
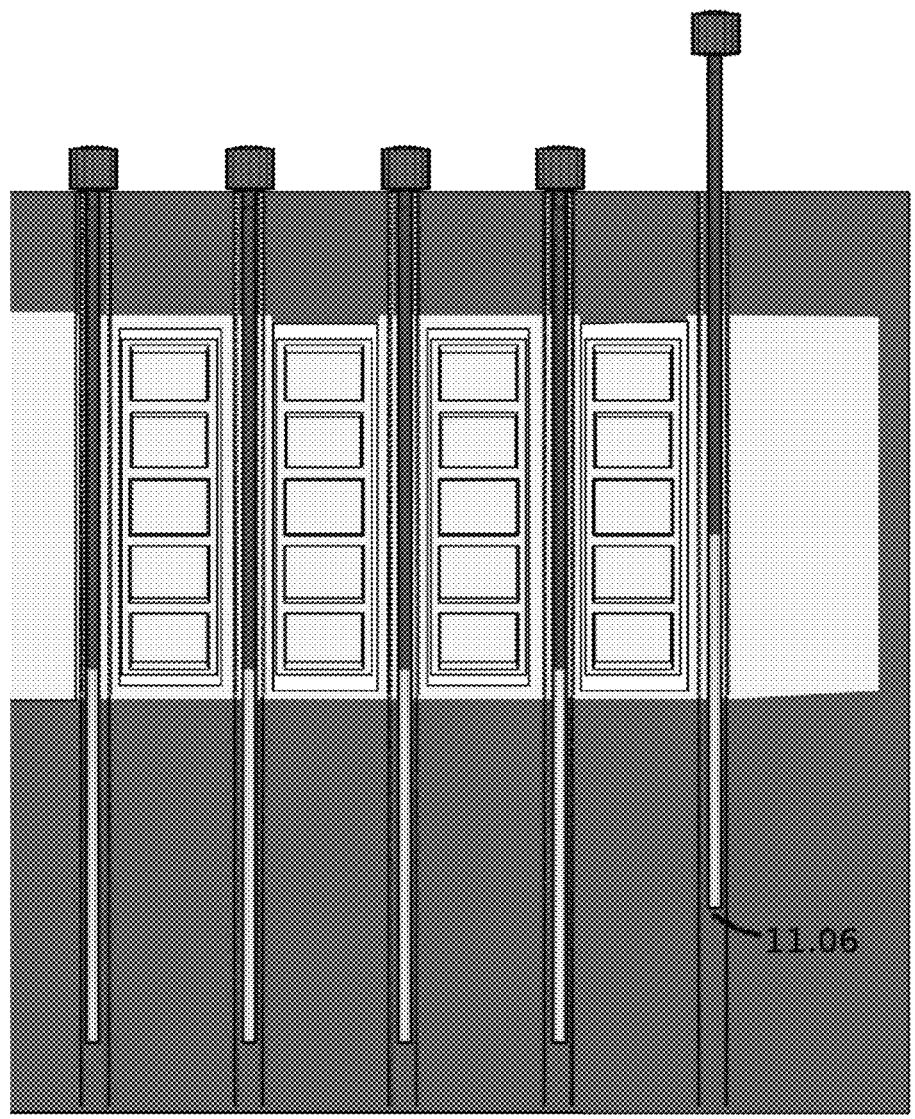
Figure 11C:
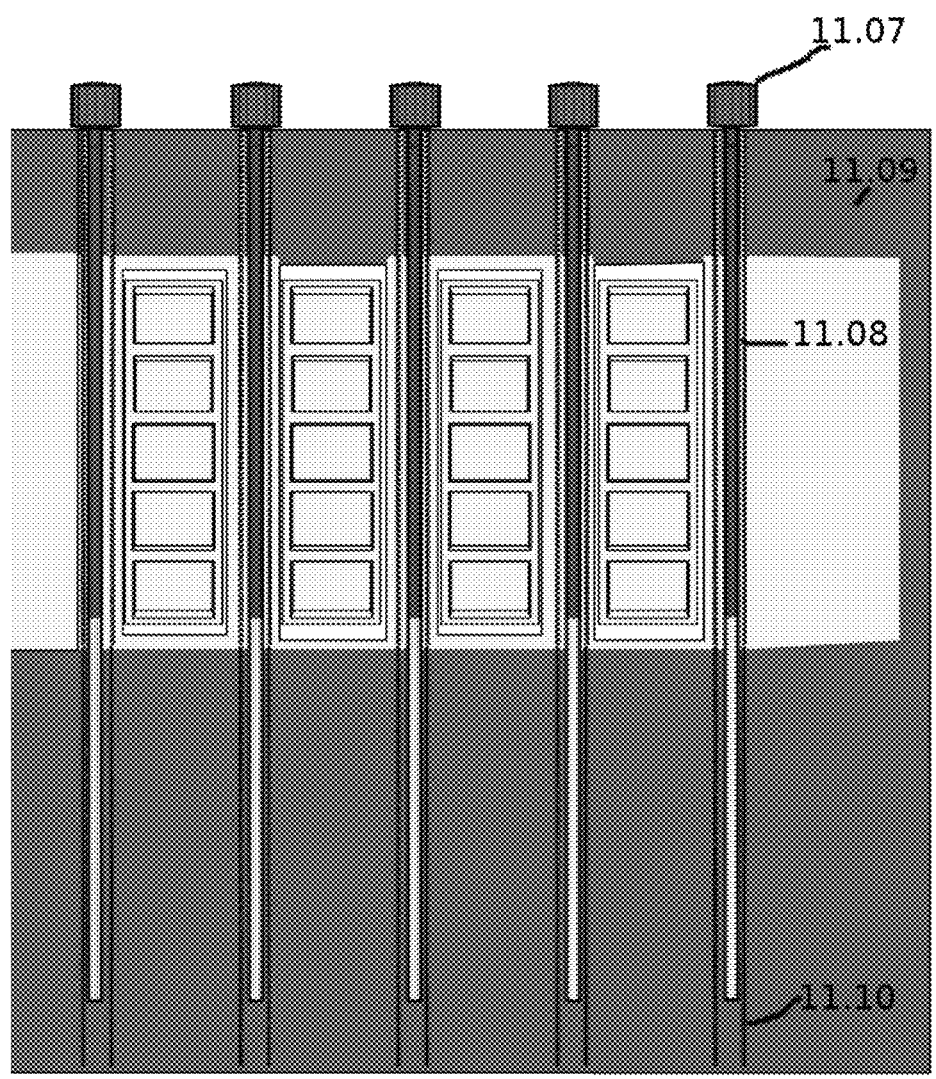

FIG. 9A also shows a bulge (9.09) near the top of the thermal conduction element which is of a larger diameter than the rest of the thermal conduction element. According to one embodiment of this invention the bulge would act as a stop such that when the SNF bearing container is dropped from the irradiation room level down into the bottom level of the SNF storage facility the bulge would make contact with the top of the roof of the irradiation room and prevent the SNF bearing container from free falling to the absolute bottom of the borehole. In this way the SNF bearing container is suspended in the air inside of the borehole and the mechanical stresses induced by the fall felt by the SNF and the SNF bearing container are greatly reduced compared to letting the SNF bearing container free fall to the bottom of the borehole. FIG. 11A through FIG. 11C illustrate this concept.

The bulge also serves the function of shielding gamma rays. The SNF bearing container is composed of a low density and low Z material (such as Aluminum) which is meant to allow a high percentage of gamma rays to escape. Should the thermal conduction element and connection piece be made of similar materials as the SNF bearing container then a significant amount of gamma radiation could travel through the top of the SNF bearing container and out of the thermal conduction element which would create low to high radiation areas near locations such as the shielded transport container and the top level of the SNF storage facility which contain the thermal conduction elements. The bulge is preferably composed of denser and higher Z materials that are more efficient at blocking gamma rays. A moderately high thermal conductivity is also an attractive feature in the bulge material selection with examples of bulge materials being Copper, Tungsten, or Lead but other materials could also be used. The bulge is therefore able to reduce the amount of gamma rays streaming from the top of the thermal conduction elements into areas where radiation is undesirable without significantly reducing the heat dissipation from the thermal conduction element to the environment.

The bulge and thermal conduction element may be two separate pieces connected by a connection piece or can be of one solid construction. The ability to interchange bulges can be advantageous given that the shorter length of the thermal conduction element during transportation in the shielded transportation container reduces the amount of material between the gamma rays created by the SNF and the area outside of the shielded transportation container which means a thicker bulge for the purposes of shielding would be desirable in this situation, while a smaller bulge may be acceptable during storage in the SNF storage facility.

Figure 10:
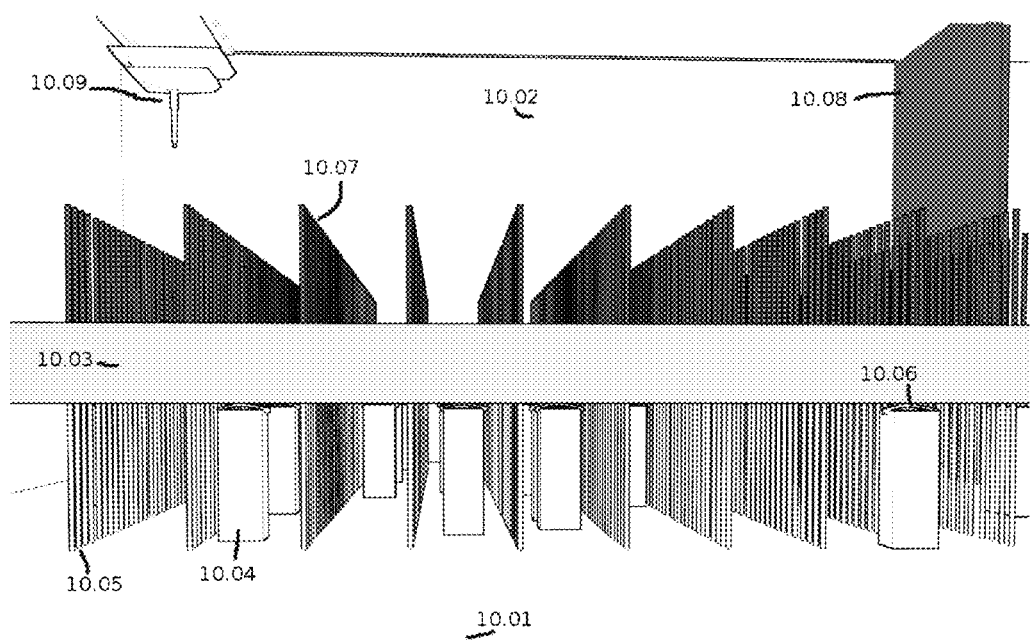
FIG. 10: Cross sectional view of most of the inside of the SNF storage facility according to one embodiment of the invention

Referring now to FIG. 10, a cutaway view of the irradiation room (10.01), top level (10.02), and the roof of the irradiation room (10.03) that separates the top level from the irradiation room is shown. The irradiation room contains boxes (10.04) full of products being irradiated by gamma rays given off by the SNF bearing containers (10.05) as the boxes are moved through the irradiation room via an overhead conveyor system (10.06). Thermal conduction elements (10.07) transport heat given off by the SNF bearing containers to the top level of the SNF storage facility so that the irradiation room and SNF inside of the SNF bearing containers do not become substantially hot. The roof of the irradiation room also serves to significantly shield the top level of the SNF storage facility from the high radiation fields found in the irradiation room. Any penetration in the roof of the irradiation room may be sealed with a plug to reduce radiation levels in the top level of the SNF storage facility when SNF bearing containers are not occupying said penetration. The hangar doors (10.08) separating the top level of the SNF storage facility from the SNF transfer bay and the overhead crane (10.09) may also be seen in FIG. 10.

Referring now to FIGS. 11A-11C, a cutaway view of the irradiation room (11.01), top level of the SNF storage facility (11.02), and the bottom level of the SNF storage facility (11.03) can be seen and the range of motion of the SNF bearing container is shown as it travels from the irradiation room to the bottom level of the SNF storage facility according to one embodiment of the present invention. In FIG. 11A the SNF bearing container (11.04) is located in the irradiation room where its gamma rays can deposit energy into boxes of products (11.05) carried through the irradiation room by a conveyor system. In FIG. 11B the SNF bearing container begins to drop through a penetration in the bottom level of the facility, known as a borehole (11.06), to lower gamma radiation reaching the irradiation room. In FIG. 11C the bulge (11.07) at the top of the thermal conduction element (11.08) collides with the roof (11.09) of the irradiation room and prevents the SNF bearing container from falling all the way to the bottom (11.10) of the borehole in the bottom level of the SNF storage facility. The bulge now acts to shield the top level of the SNF storage facility, above the roof of the irradiation room, from gamma rays and the foundational material in the bottom level of the SNF storage facility acts to shield the irradiation room from gamma rays.

To begin the SNF storage process according to one embodiment of the invention a SNF rod or SNF assembly is taken from the nuclear reactor or spent fuel pool and loaded into the SNF bearing container. The SNF bearing container can contain rigid supports that mimic the spacer grids or support plates inside of conventional nuclear fuel assemblies and nuclear reactor cores. These rigid supports guide the SNF into the container during loading and provide support to minimize seismic damage or fall damage during an earthquake or fuel drop accident. The SNF bearing container is then filled with the fill material and sealed. In the preferred embodiment the SNF bearing container is composed of an Aluminum tube that is roughly 1 centimeter thick, the thermal conduction element is composed of a solid Copper rod, and the fill material is a resin which hardens during the loading process such that it encases the SNF in a pseudo-glassification process and acts as a large barrier to fission product release into the environment during accident scenarios. A connection piece composed of Aluminum is implemented in the preferred embodiment to join the SNF bearing container and the thermal conduction element such that the length of the thermal conduction elements may be interchanged throughout the transportation and storage process.

The SNF bearing container is placed into a shielded transport container similar to the SNF storage/transportation containers currently implemented in many nuclear power plants, but with a lower fuel density and higher thermal heat removal capacity designed to allow easier movement of younger hotter SNF than current nuclear power industry standards. The transport container is moved to the transfer bay near the top level of the facility via a lifting vehicle that can carry the weight of the shielded transport container. The lifting vehicle is similar to those already used for dry cask storage systems at nuclear power plants. The ability of the shielded transport container to dissipate the high heat loads created by the young SNF is greatly enhanced by incorporating slots for the thermal conduction elements to penetrate into the shielded transport container and make contact with the SNF or the SNF bearing containers. These slots can be sealed or plugged in the event of only a partially full shielded transport container to further reduce the likelihood of contamination of the environment and to lower radiation levels outside of the shielded transport container. The thermal conduction elements used in the transportation process can be of a different design than those used in the facility itself and a large bulge in the thermal conduction element located near the area of the slot would further reduce the amount of gamma radiation escaping outside of the shielded transport container. The use of thermal conduction heat transfer out of the shielded transport container is an advancement that substantially increases heat dissipation and reduces complexity compared to typical dry storage designs that rely heavily on convective heat transfer. Further the low density of fuel in the shielded transport container reduces costs and complexity associated with preventing criticality accidents since a critical geometry becomes more difficult to achieve with less SNF present. The use of lightweight shielded transport containers and remote handling could also increase the efficiency of the SNF transportation process when combined with computer automation systems.

In another embodiment of the invention the SNF is placed into traditional SNF transportation containers and taken to the SNF transfer bay of the SNF storage facility. In this embodiment the SNF is placed into the SNF bearing containers at the SNF storage facility rather than letting the encapsulation process occur at the spent fuel pool or any other location at the nuclear power plant.

The SNF bearing containers are loaded into the SNF storage facility via an overhead crane system. The preferred embodiment incorporates SNF bearing containers stored on an individual fuel rod basis to enhance the fraction of recoverable gamma radiation. The SNF storage facility may contain an area that has a higher storage density of SNF bearing containers such that gamma rays are no longer harvested substantially efficiently but substantially inexpensive storage is still provided by no longer placing the SNF bearing containers in rigid rows but rather clustering them closer together in the preferred embodiment of this invention. Since storing SNF in rows on an individual fuel rod basis takes up significantly more space than having rows of SNF stored on an individual fuel assembly basis it can be advantageous to only store a few reactor refuelings worth of SNF in order to reduce the size and cost of the SNF storage facility. In this scenario one refuelings worth of SNF bearing containers would be placed into the SNF storage facility every time the nuclear reactor is refueled and one refuelings worth of SNF bearing containers would be simultaneously taken out of the SNF storage facility and placed into higher density storage locations that are not as focused on harvesting gamma rays but still provide inexpensive SNF storage. The locations/placement of the younger and older SNF bearing containers inside of the SNF storage facility would be used to customize the radiation levels in different areas of the irradiation room.

In another embodiment of the present invention the SNF bearing container may have the SNF taken out of it and the SNF bearing container may have new SNF placed into it such that the SNF bearing container is reusable. In such an embodiment new SNF would be placed into the SNF storage facility every time the nuclear reactor is refueled and an equivalent amount of SNF within the SNF containers would be simultaneously taken out of the SNF storage facility and placed into higher density storage locations that are not as focused on harvesting gamma rays but still provide inexpensive SNF storage.

In the preferred embodiment sections of the irradiation room have younger, more radioactive, SNF in their SNF bearing containers than other sections of the irradiation room. The intensity and energy spectrum of the neutrons and gamma rays would therefore be different in each section of the irradiation room, depending on the age of the SNF contained in a particular section. Some products will require the higher dose rates associated with the younger SNF and other more fragile products will need to avoid these higher radiation level regions of the irradiation room. This provides irradiation plant operators with substantial flexibility and offers customers with products requiring irradiation more processing options in terms of radiation dose control. A portion of the irradiation room could be equipped with a larger conveyor system than the other portions of the irradiation room to accommodate the treatment of larger products.

The thermal conduction elements/SNF bearing containers (in their withdrawn, "radiation on", configuration that keeps the SNF bearing container inside of the irradiation room) may be held in place by a simple latch system. Unlatching the system causes the SNF bearing container to drop into the borehole storage location underneath of it on the bottom level of the SNF storage facility (which can be referred to as the "radiation off" configuration). The fall is softened through the use of padding, tolerancing, and/or a spring such that the container and the SNF inside of it is not damaged from the force of the fall. The bulge located at the top of the thermal conduction element could also be configured to prevent the SNF bearing container from unnecessarily colliding with the bottom of the borehole during its motion from the "radiation on" to the "radiation off" position by suspending the SNF bearing container above the bottom of the borehole. To return all the containers to their shielded "radiation off" positions as quickly as possible in the event of an operational complication, an operator can unhitch all the latches at the same time. To return the containers to their unshielded positions the overhead cranes would lift the thermal conduction elements (which are still partially exposed on the top floor) up until the latch resets itself and holds the SNF bearing container in place in its "radiation on" position. Provisions are made such that the likelihood of over lifting the container and accidentally exposing the top level of the facility to high gamma radiation at an unsafe time when workers could be present would be substantially minimized. The thermal conduction pathway coupled to the SNF bearing container contains visibly distinguishable characteristics, such as being a different color, which differentiates it from the SNF bearing container such that workers can be alerted to whether the irradiation room contains high levels of radiation by distinguishing whether the SNF bearing containers or the thermal conduction elements are in the irradiation room. The workers would also be able to tell if the SNF bearing container was still present in the irradiation room by seeing how much length of the thermal conduction element is exposed on the top level of the SNF storage facility.

Convective heat transfer also occurs and active heat removal systems such as filtered HVAC systems may be employed in the preferred embodiment of this invention for an extra margin of safety and for maintaining product integrity when certain sterilizable products can not be exposed to higher temperatures that the SNF itself could withstand. Vents can be strategically placed to intake cold air and reject warmer air to assist in the convective heat transfer occurring inside of the facility in order to cool the irradiation room.

The SNF bearing containers can have variable residency times within the facility. Depending on market demands the facility can be constructed and modified to substantially maximize gamma ray output or substantially maximize SNF storage. This can be accomplished by changing the spacing between the rows of SNF bearing containers and whether the SNF bearing containers are on an assembly or fuel rod basis. The fuel assembly basis SNF bearing container is able to store significantly more SNF in the same area compared to the fuel rod basis SNF bearing container at the expense of not letting as large of a percentage of the gamma rays escape into the irradiation room due to the SNF in the center of the assembly depositing a substantial portion of its gamma ray energy into the surrounding material/SNF at the center of the assembly.

SNF can be shuffled out of the facility after a significant amount of its gamma radiation has decayed away over the course of years. These older SNF bearing containers can then be placed into more conventional dry storage systems or shipped off to a permanent SNF repository. In another embodiment of the invention the SNF can remain in the facility indefinitely and intermittently be repackaged into new SNF bearing containers should degradation issues occur over the course of time. In another embodiment of the invention the SNF can be removed from the SNF bearing containers and repackaged into alternative SNF storage technologies.

The concrete and other components in the irradiation room and bottom level of the SNF storage facility may be doped with Boron, Gadolinium, or another neutron poison to further increase criticality safety margins if desired in the preferred embodiment.

The SNF storage facility is located on-site inside of the secure land areas found at nuclear power plants in the preferred embodiment. The SNF storage facility could also be located off-site away from the nuclear power plants in another embodiment of this invention. The SNF bearing containers could also be used in locations outside of the SNF storage facility in yet another embodiment of this invention. In one embodiment of the present invention the encapsulated nuclear fuel (AKA "SNF bearing containers") could be individually shipped to various off site locations to be used as a gamma ray source in the same manner in which other radioactive sources are sent to and used at hospitals, universities, food processing facilities, etc.

The invention claimed is:
1. A method of managing spent nuclear fuel, comprising;
placing spent nuclear fuel (SNF) that includes radioisotopes into a plurality of SNF bearing containers on an individual SNF rod or individual SNF assembly basis, the SNF bearing containers each
comprising a barrier having a thickness of between 0.0001 centimeters and 15 centimeters, inclusive, between the SNF and an area outside of the SNF bearing containers and
configured to
allow the release of gamma radiation from the SNF inside of the SNF bearing containers and
prevent the release of the radioisotopes, contained in the SNF which produce the gamma radiation, to the area outside of the SNF bearing containers;
placing the SNF bearing containers in multiple locations within an irradiation room within a SNF storage facility such that the SNF bearing containers are arranged into more than two rows;
utilizing a plurality of independent conveyor systems to carry medical products meant to be irradiated through different dose rate areas of the irradiation room,
wherein the dose rate areas are defined by a respective area in between, or adjacent to, rows of SNF bearing containers in the irradiation room;
using an SNF storage facility that contains
a level above the irradiation room and
a level below the irradiation room that provides an associated borehole storage location for each individual SNF storage container;
individually connecting thermal conduction elements to the top of each individual SNF bearing container, where each individual SNF bearing container has a separate thermal conduction element, and each thermal conduction element is sufficiently long to enable the top of the thermal conduction element to protrude out of the irradiation room and into the level above the irradiation room
while the SNF bearing container that the thermal conduction element is connected to is in its associated borehole storage location below the irradiation room; and
moving the individual SNF bearing container between the level above the irradiation room, the irradiation room, and the level below the irradiation room by
connecting a crane located in the level above the irradiation room to the thermal conduction element associated with the individual SNF bearing container and
pulling or pushing the thermal conduction element up or down when it is desired to move the individual SNF bearing container outside of the irradiation room or into the irradiation room to affect the amount of radiation in the irradiation room.

2. A method of managing spent nuclear fuel, comprising;
placing spent nuclear fuel (SNF) that includes radioisotopes into a plurality of SNF bearing containers on an individual SNF rod or individual SNF assembly basis, the SNF bearing containers each
   comprising a barrier having a thickness of between 0.0001 centimeters and 15 centimeters, inclusive, between the SNF and an area outside of the SNF bearing containers and
   configured to
      allow the release of gamma radiation from the SNF inside of the SNF bearing containers and
      prevent the release of the radioisotopes, contained in the SNF which produce the gamma radiation, to the area outside of the SNF bearing containers;
placing the SNF bearing containers in multiple locations within an irradiation room within a SNF storage facility such that the SNF bearing containers are arranged into more than two rows;
utilizing a plurality of independent conveyor systems to carry medical products meant to be irradiated through different dose rate areas of the irradiation room,
   wherein the dose rate areas are defined by a respective area in between, or adjacent to, rows of SNF bearing containers in the irradiation room;
loading SNF less than 20 months after the SNF has been discharged from a nuclear reactor into SNF bearing containers that contain rigid supports;
using the rigid supports to guide the SNF into the SNF bearing containers during loading;
using a lifting vehicle and a shielded transport container to transport the SNF bearing containers to the SNF storage facility;
coupling the SNF bearing containers to thermal conduction elements such that the thermal conduction elements are directly above the SNF;
transporting the SNF bearing containers to the SNF storage facility and
cooling the SNF during transportation of the SNF to the SNF storage facility by allowing a thermal conduction element coupled to the SNF bearing container directly above the SNF to penetrate out of the top of the shielded transport container; and
lifting the coupled SNF bearing container and thermal conduction element by the thermal conduction element out of an opening in the shielded transport container and
lowering the SNF bearing container to a penetration in the irradiation room.

3. A method of managing spent nuclear fuel, comprising;
placing spent nuclear fuel (SNF) that includes radioisotopes into a plurality of SNF bearing containers on an individual SNF rod or individual SNF assembly basis, the SNF bearing containers each
   comprising a barrier having a thickness of between 0.0001 centimeters and 15 centimeters, inclusive, between the SNF and an area outside of the SNF bearing containers and
   configured to
      allow the release of gamma radiation from the SNF inside of the SNF bearing containers and
      prevent the release of the radioisotopes, contained in the SNF which produce the gamma radiation, to the area outside of the SNF bearing containers;
placing the SNF bearing containers in multiple locations within an irradiation room within a SNF storage facility such that the SNF bearing containers are arranged into more than two rows;
utilizing a plurality of independent conveyor systems to carry medical products meant to be irradiated through different dose rate areas of the irradiation room,
   wherein the dose rate areas are defined by a respective area in between, or adjacent to, rows of SNF bearing containers in the irradiation room;
using a SNF storage facility that contains more than two levels including a top level of the SNF storage facility that is above the irradiation room and a bottom level of the SNF storage facility that is below the irradiation room;
aligning penetrations between different levels of the SNF storage facility;
sizing the penetrations such that only one SNF bearing container can fit into each penetration;
maneuvering the SNF bearing containers between the different levels of the SNF storage facility through the aligned penetrations;
coupling a SNF bearing container to a thermal conduction element directly above the SNF bearing container
   where the thermal conduction element includes a bulge that is
      of a larger diameter than the rest of the thermal conduction element and
      configured such that lowering the SNF bearing container into the bottom level of the SNF storage facility causes the bulge to
         collide with an aligned penetration associated with the SNF bearing containers location in the SNF storage facility between the irradiation room and the top level of the SNF storage facility and
         prevents the SNF bearing container from being lowered any further and
         suspends the SNF bearing container above the bottom of the bottom level of the SNF storage facility and
         prevents the SNF bearing container from colliding with the bottom of the bottom level of the SNF storage facility during a free fall; and
shielding the top level of the SNF storage facility by using the bulge on the thermal conduction element to plug a penetration associated with the top level of the SNF storage facility.

* * * * *